US008883952B2

(12) United States Patent
Cheong et al.

(10) Patent No.: US 8,883,952 B2
(45) Date of Patent: *Nov. 11, 2014

(54) OPTICALLY ANISOTROPIC COMPOUND AND RESIN COMPOSITION COMPRISING THE SAME

(75) Inventors: Jaeho Cheong, Daejeon (KR); Minjin Ko, Daejeon (KR); Bumgyu Choi, Seo-gu (KR); Kiyoul Lee, Daejeon (KR); YunBong Kim, Daejeon (KR); Myungsun Moon, Daejeon (KR); Daeho Kang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 301 days.

This patent is subject to a terminal disclaimer.

(21) Appl. No.: 12/451,835

(22) PCT Filed: Jun. 4, 2008

(86) PCT No.: PCT/KR2008/003127
§ 371 (c)(1),
(2), (4) Date: Dec. 3, 2009

(87) PCT Pub. No.: WO2008/150099
PCT Pub. Date: Dec. 11, 2008

(65) Prior Publication Data
US 2010/0105816 A1    Apr. 29, 2010

(30) Foreign Application Priority Data
Jun. 5, 2007    (KR) .................. 10-2007-0055016

(51) Int. Cl.
*C08G 77/24*    (2006.01)
*C07F 7/08*    (2006.01)

(52) U.S. Cl.
CPC ...................... *C07F 7/0818* (2013.01)
USPC ........................................ 528/42

(58) Field of Classification Search
USPC ........................................ 528/42
See application file for complete search history.

(56) References Cited

U.S. PATENT DOCUMENTS

| 3,770,790 | A  | * | 11/1973 | Clark ............................ 556/447 |
| 2006/0046479 | A1 | * | 3/2006 | Rajagopalan et al. ........ 438/683 |
| 2010/0190938 | A1 | * | 7/2010 | Yano et al. ................. 526/124.3 |
| 2010/0190942 | A1 | * | 7/2010 | Hosaka et al. ................ 526/128 |

FOREIGN PATENT DOCUMENTS

| EP | 1 160 250 | * | 5/2001 |
| JP | 51-48794 | | 4/1976 |
| JP | 02-129211 | | 5/1990 |
| JP | 05-245789 | | 12/1993 |
| JP | 06-228559 | | 8/1994 |
| JP | 06-319970 | | 11/1994 |
| JP | 08-110402 | A | 4/1996 |
| JP | 2000-044614 | | 2/2000 |
| JP | 2001-335586 | | 12/2001 |
| JP | 2004-035347 | | 2/2004 |
| JP | 2006-265511 | | 10/2006 |
| JP | 2007-051071 | | 3/2007 |
| WO | WO 2005/109473 | | 11/2005 |
| WO | WO 2006/075882 | | 7/2006 |
| WO | WO 2006/075883 | | 7/2006 |
| WO | WO 2006/122630 | | 11/2006 |
| WO | WO 2006/129773 | A1 | 12/2006 |
| WO | WO 2007/018280 | A1 | 2/2007 |

OTHER PUBLICATIONS

Gevorgyan, J. Am. Chem. Soc., 121(27) (1999) 6391-6402.*
JP 2007 051071 machine translation (2007).*
Fink ("Silylated polyphenyl ethers. Their preparation and some physical properties", Helvetia Chimica Acta, 56(1) 355-63 (1973)).*
Yamaji et al. ("C-Si bond dissociation in highly excited triplet states of phenylbenzylphenylsilanes studied by stepwise two-color laser photolysis in solution", Chemical Physics Letters, 438(4-6) 229-233 (2007)).*
Yashida et al. ("Gas phase cation-Π complexation of cyclic and acyclic organosilicon compounds: electrospray mass spectrometry analysis and theoretical investigation by ab initio molecular orbital calculations" Journal of the Chemical Society, Dalton Transactions (9) 1489-1505 (2001)).*
Murphy et al. ("Studies in organosilicon chemistry. XLIII. An invenstigation of silicon-containing s-triazines", Journal of Organic Chemistry, (27) 1486-8 (1962)).*
Babu ("Silicon-modified polyimides: Synthesis and properties", Polyimides: Synth., Charact., Appl., [Proc.Tech. Conf. Polyimides], 1st (1984), Meeting Date 1982, vol. 1, 51-66, Editor(s): Mittal, K. L. Plenum: New York, N.Y.).*
Bhattacharya et al. ("Organosilicon compounds. XLIII. Preparation of aryl sulfones by desilylation or destannylation", Journal of the Chemical Society [Section] C: Organic, (10) 1367-9 (1969)).*
Kang, D. J. et al.; "Direct photofabrication of refractive-index-modulated multimode optical waveguide using photosensitive sol-gel hybrid materials." Applied Physics Letters. 2005, vol. 87, No. 22, pp. 221106/1-221106/3.
Grogger, C. et al.; "Electrochemical synthesis of symmetrical difunctional disilanes as precursors for organofunctional silanes"; Journal of Organometallic Chemistory 2006, vol. 691, No. 1-2 pp. 105-110.
Cherkaoui et al. "Ferroelectric Liquid-Crystalline Compounds containing a sulfinyl group as unique source of chirality: Asymmetric synthesis and mesomorphic properties", Chem. Mater., vol. 6, pp. 2026-2039, 1994.
Yoshino et al. "Photoluminescence, Electroluminescence, lasing and novel characteristics in photonic crystal, synthetic opal, of conducting polymers, polyacetylene derivatives", Mol. Cryst, Liq. Cryst., vol. 332, pp. 253-262, 1998.
Sakaguci et al. Synthesis and properties of F-containing poly(diphenylacetylene) membranes), Macromolecules, vol. 38, pp. 8327-8332, 2005.

* cited by examiner

*Primary Examiner* — Kuo-Liang Peng
(74) *Attorney, Agent, or Firm* — McKenna Long & Aldridge, LLP

(57) ABSTRACT

Disclosed is a silicon containing compound represented by Formula 1 which has high optical anisotropy and high compatibility with a polymer resin. Also, a resin composition including the compound and a polymer resin, and an optical member including the resin composition are disclosed. Since the silicon containing compound represented by Formula 1 has high compatibility with a polymer resin and high optical anisotropy, in the case of an optical member obtained by using a polymer resin composition including the silicon containing compound, there is no phase separation, and it is possible to achieve a required optical characteristic with only a small amount thereof.

20 Claims, 2 Drawing Sheets

OPTICALLY ANISOTROPIC COMPOUND AND RESIN COMPOSITION COMPRISING THE SAME

This application claims the benefit of PCT/KR2008/003127 filed on Jun. 4, 2008, along with Korean Patent Application No. 10-2007-0055016 filed on Jun. 5, 2007, both of which are hereby incorporated herein by reference for all purposes in their entirety.

TECHNICAL FIELD

The present invention relates to a silicon containing compound having high compatibility with a polymer resin and high optical anisotropy. Also, the present invention relates to a resin composition including the compound, and an optical member including the resin composition.

BACKGROUND ART

Recently, with the development of the electronics industry, the use of a polymer resin for optical use has rapidly increased. For example, the demand for various polymer materials for optical use, such as an optical disc substrate used as a storage medium, an optical lens, an optical fiber used for optical communication, a fresnel lens for a projection screen, a prism sheet used in a liquid crystal display, a protective film for a polarizing plate, a compensation film, etc., has been rapidly increased.

Such polymer resins for optical use are usually required to be optically isotropic, but a polymer resin of a final product may be anisotropic due to its own structure or stress during the process. Also, an optical resin, when inserted in a multi-layered structure, may have optical anisotropy by thermal expansion/contraction between respective layers.

When a film, lens, etc. with such optical anisotropy exists in an optical path, a property of the phase may be changed, thereby adversely affecting signal reading. Therefore, it is preferable to use an optical member including an optical resin of which anisotropy is reduced as much as possible.

On the other hand, optical birefringence may be artificially given. For example, in the case of a liquid crystal display, the contrast at an inclined viewing angle may be degraded due to optical birefringence caused by the liquid crystal and a polarizing film. In order to solve this problem, a polymer resin having optical anisotropy with a certain direction may be used to compensate the birefringence caused by the liquid crystal and the polarizing film, thereby improving a viewing angle. In the case of a polymer resin for optical use as mentioned above, the optical characteristic is required to be controlled in a required direction.

As a conventional technology of controlling the optical characteristic of a polymer, a birefringence control method through adjustment of the structure of a polymer resin, such as Japanese Laid-Open Patent Nos. 1990-129211 and 2000-044614, has been known. However, the method has a problem in that the composition of a monomer of a copolymer is required to be changed to control the birefringence, and the change in the composition of the monomer may change other physical properties of the polymer resin.

Also, as a birefringence control method of a polymer resin, methods of adding an anisotropic material have been known. Japanese Laid-Open Patent No. 2004-035347 disclosed a method of introducing a needle-shaped inorganic particle as an anisotropic material to adjust an optical characteristic. However, in the case of an inorganic fine particle, it is difficult to uniformly disperse the particle in a solvent due to low solubility in the solvent, and high density, and there is a possibility that the particle is subject to aggregation due to low stability, thereby reducing the transparency of the polymer resin. Also, Japanese Laid-Open Patent No. Hei 8-110402 disclosed a method of adjusting the optical characteristic of a polymer resin by adding a low-molecular organic compound. In general, compounds with high anisotropy have disadvantages, such as high crystallinity, low solubility in a solvent, and low compatibility with the polymer resin. Thus, the compounds, when mixed, may be precipitated by crystallization, and may be not dissolved in a solvent. However, there is no specific solution for such problems.

DISCLOSURE

Technical Problem

Therefore, the present invention has been made in view of the above-mentioned problems. The present invention provides an optically anisotropic compound which has high optical anisotropy and high solubility in a solvent, can effectively control the optical characteristic of a polymer resin with only a small amount thereof, and does not cause a problem, such as precipitation, due to high compatibility with the polymer resin.

Also, the present invention provides a resin composition including the optically anisotropic material and the polymer resin.

Technical Solution

In accordance with an aspect of the present invention, there is provided a silicon containing compound represented by Formula 1:

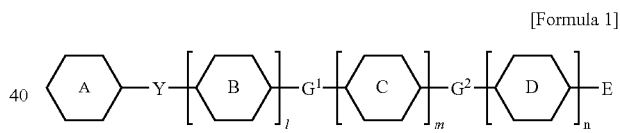

[Formula 1]

In Formula 1,

represents

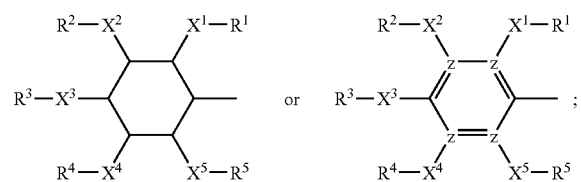

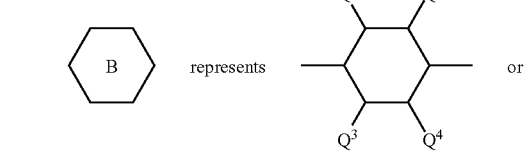

-continued

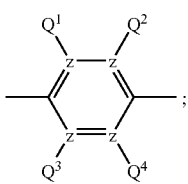

 represents 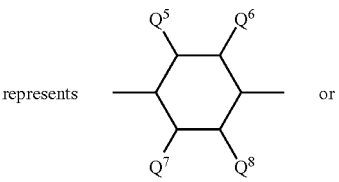 ;

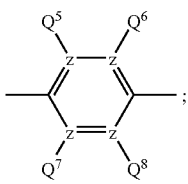

 represents 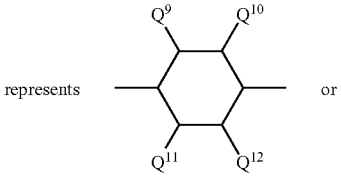 ;

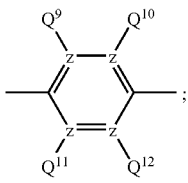

each of $Q^1$ to $Q^{12}$ independently represents —H, —F, —Cl, —Br, —I, —CN, —CF$_3$, —OCF$_3$, —OR$^6$, —NHR$^6$, —NR$^6$R$^6$ or —C(=O)R$^6$;

Z represents C or N, and herein, if Z is N, there is no bond with corresponding $Q^1$ to $Q^{12}$;

each of l, m and n independently represents an integer of 0 to 2, and l+m+n represents an integer equal to or greater than 1;

each of Y, $G^1$ and $G^2$ independently represents —(CH$_2$)$_r$SiW$^1$W$^2$(CH$_2$)$_s$—, —O—, —NR$^6$—, —S—, —SO—, —SO$_2$—, —(CH$_2$)$_q$—, —CH=CH—, —C≡C—, —C(=O)O(CH$_2$)$_q$—, —OC(=O)(CH$_2$)$_q$—, —(CH$_2$)$_q$C(=O)O—, —(CH$_2$)$_q$OC(=O)—, —C(=O)(CH$_2$)$_q$—, —(CH$_2$)$_q$C(=O)—, —C(=O)NR$^6$—, NR$^6$C(=O)—, —C(=O)S—, or —SC(=O)—, q represents an integer of 0 to 5, each of r and s independently represents an integer of 0 to 2;

E represents —H, —F, —Cl, —Br, —I, —CN, —NCO, —NCS, —SiW$^1$W$^2$R$^6$, —R$^6$, —N(R$^6$)$_2$, —OR$^6$, —CF$_3$, or —OCF$_3$;

each of $X^1$ to $X^5$ independently represents —SiW$^1$W$^2$—, —O—, —NR$^6$—, —S—, —SO—, —SO$_2$—, —(CH$_2$)$_p$—, —C(=O)NR$^6$—, —NR$^6$C(=O)—, —NR$^6$C(=O)NR$^6$—, —C(=O)O—, —OC(=O)—, or —OC(=O)O—, and p represents an integer of 0 to 2;

$W^1$ represents —R$^7$, —OR$^7$, —NHR$^7$, or —N(R$^7$)$_2$;
$W^2$ represents —R$^8$, —OR$^8$, —NHR$^8$, or —N(R$^8$)$_2$;

each of $R^1$ to $R^8$ independently represents —H, C$_1$~C$_{20}$ alkyl, C$_1$~C$_{20}$ fluoroalkyl, C$_2$~C$_{20}$ alkenyl, C$_2$~C$_{20}$ fluoroalkenyl, C$_2$~C$_{20}$ alkynyl, C$_2$~C$_{20}$ fluoroalkynyl, —(CH$_2$CH$_2$O)$_t$CH$_3$, —(CH$_2$CHCH$_3$O)$_t$CH$_3$, or —(CHCH$_3$CH$_2$O)$_t$CH$_3$, and t represents an integer of 1 to 5; and at least one of Y, $G^1$, $G^2$, E, and $X^1$ to $X^5$ is a Si containing substituent, and herein, as the Si containing substituent, in Y, $G^1$ and $G^2$, —(CH$_2$)$_r$SiW$^1$W$^2$(CH$_2$)$_s$— is introduced, in E, —SiW$^1$W$^2$R$^6$ is introduced, and in $X^1$ to $X^5$, —SiW$^1$W$^2$— is introduced.

In accordance with another aspect of the present invention, there is provided a resin composition including a polymer resin and the silicon containing compound represented by Formula 1.

In accordance with a further aspect of the present invention, there is provided an optical member including the resin composition.

Advantageous Effects

A silicon containing compound represented by Formula 1 of the present invention has high compatibility with a polymer resin and high optical anisotropy. Accordingly, in the case of an optical member obtained by using a polymer resin composition including the silicon containing compound represented by Formula 1, there is no phase separation, and it is possible to achieve a required optical characteristic with only a small amount thereof.

BEST MODE

Figure 1:
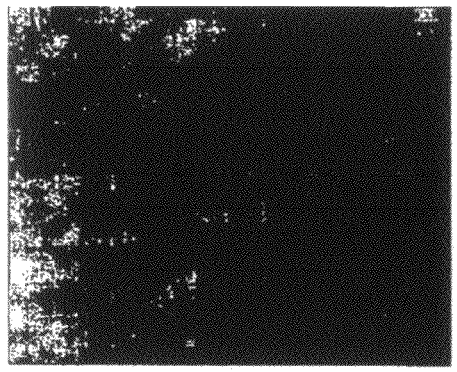
FIGS. 1 and 2 are optical microscopic photographs (×5) showing the results of the compatibility tests according to Examples 3 and 4.

Hereinafter, the present invention will be described in detail.

The compound represented by Formula 1 of the present invention is an optically anisotropic compound having refractive anisotropy of 0.2 or more, and necessarily has at least one silicon group. In Formula 1, at least one of Y, $G^1$, $G^2$, E, and $X^1$ to $X^5$ is a Si containing substituent. Specifically, as the Si containing substituent, in Y, $G^1$ and $G^2$, —(CH$_2$)$_r$SiW$^1$W$^2$(CH$_2$)$_s$— is introduced, in E, —SiW$^1$W$^2$R$^6$ is introduced, and in $X^1$ to $X^5$, —SiW$^1$W$^2$— is introduced.

In Formula 1 of the present invention, examples of C$_1$~C$_{20}$ alkyl of $R^1$ to $R^8$ include linear or branched alkyls, such as —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, etc., but the present invention is not limited thereto. Also, in Formula 1, C$_1$~C$_{20}$ fluoroalkyl of $R^1$ to $R^8$ includes at least one fluorine group substituting for hydrogen of the alkyl group as defined above.

Also, in Formula 1, examples of C$_2$~C$_{20}$ alkenyl of $R^1$ to $R^8$ include linear or branched alkenyls, such as —CH=CH$_2$, —CH═CHCH$_3$, —CCH$_3$═CH$_2$, —CH$_2$CH═CH$_2$, —CH═CHCH$_2$CH$_3$, —CH═C(CH$_3$)$_2$, —CCH$_3$═CHCH$_3$, —CH$_2$CH═CHCH$_3$, —CH$_2$CCH$_3$═CH$_2$—CHCH$_3$CH═CH$_2$ CH$_2$CH$_2$CH═CH$_2$, etc., but the present invention is not limited thereto. Also, in Formula 1, C$_2$~C$_{20}$ fluoroalkenyl of R$^1$ to R$^8$ includes at least one fluorine group substituting for hydrogen of the alkenyl group as defined above.

Also, in Formula 1, examples of C$_2$~C$_{20}$ of R$^1$ to R$^8$ include linear or branched alkynyls, such as —C≡CH, —CH$_2$C≡CH, —C≡CCH$_3$, —CH$_2$CH$_2$C≡CH, —CHCH$_3$C≡CH, —CH$_2$C≡CCH$_3$, —C≡CCH$_2$CH$_3$, etc., but the present invention is not limited thereto. Also, in Formula 1, C$_2$~C$_{20}$ fluoroalkynyl of R$^1$ to R$^8$ includes at least one fluorine group substituting for hydrogen of the alkynyl group as defined above.

Also, in Formula 1, l+m+n represents an integer equal to or greater than 1, preferably an integer of 1 to 4, and more preferably an integer of 1 to 3.

The compound represented by Formula 1 of the present invention is easily mixed with various polymer resins, and has high solubility, even at low temperatures. In addition, the compound is physically and chemically stable under the condition where a liquid crystal display device is usually used, and is stable under heat and light.

Therefore, the compound represented by Formula 1 may be mixed with various polymer resins to control the optical characteristic of a polymer resin.

Specific examples of the compound represented by Formula 1 are as follows, but the present invention is not limited thereto.

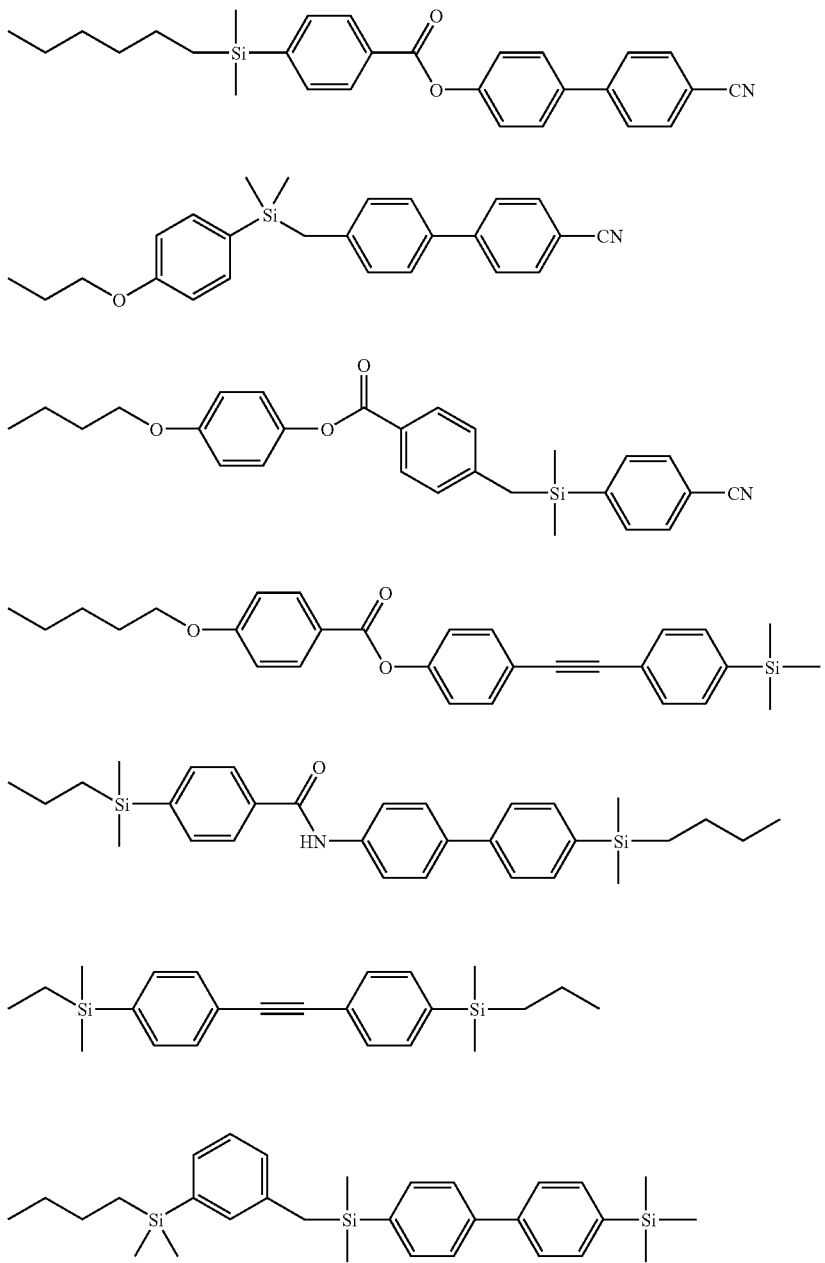

Hereinafter, the method of preparing the compound represented by Formula 1 will be described. However, the Reaction Schemes are illustrative only and do not limit the method.

The compound represented by Formula 1 may be prepared by Reaction Scheme 1.

[Reaction Scheme 1]

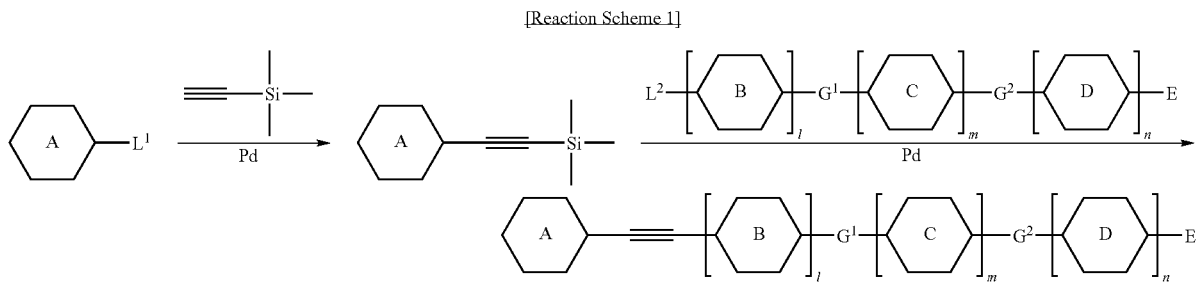

In Reaction Scheme 1, ring A, ring B, ring C, ring D, l, m, n, $G^1$, $G^2$, and E are the same as defined in Formula 1, and each of $L^1$ and $L^2$ independently represents a living group, such as halide, mesylate, tosylate, or triflate.

In Reaction Scheme 1, acetylenes such as trimethylsilylacetylene and Pd catalyst may be used to prepare the tolane compound.

Also, the compound represented by Formula 1 may be prepared by Reaction Scheme 2.

[Reaction Scheme 2]

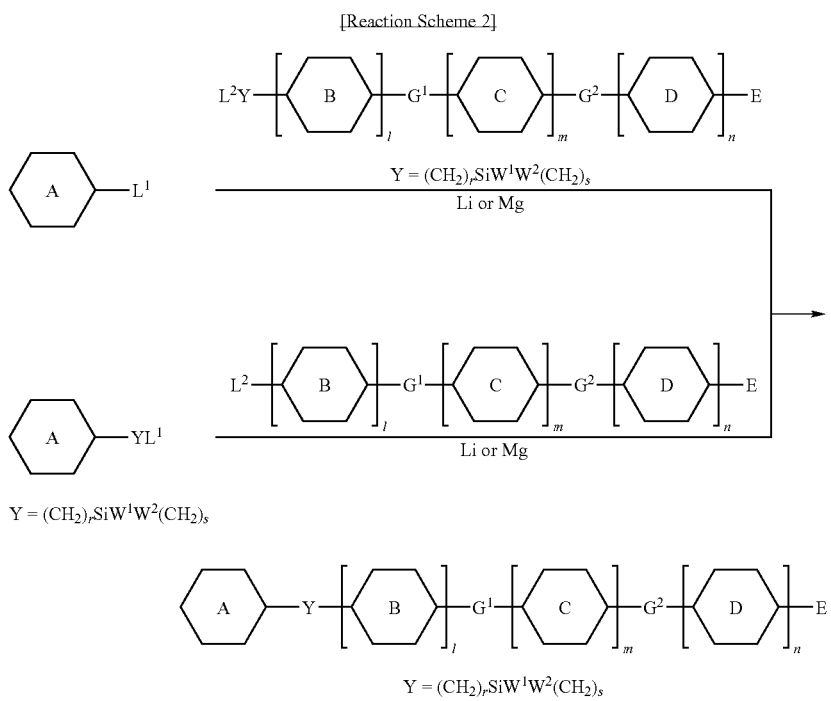

In Reaction Scheme 2, ring A, ring B, ring C, ring D, l, m, n, $W^1$, $W^2$, r, s, $G^1$, $G^2$ and E are the same as defined in Formula 1, each of $L^1$ and $L^2$ is the same as defined in Reaction Scheme 1, and Li or Mg represents a metal capable of forming anions, such as Li, n-BuLi, Mg, etc.

Also, the compound represented by Formula 1 may be prepared by Reaction Scheme 3.

[Reaction Scheme 3]

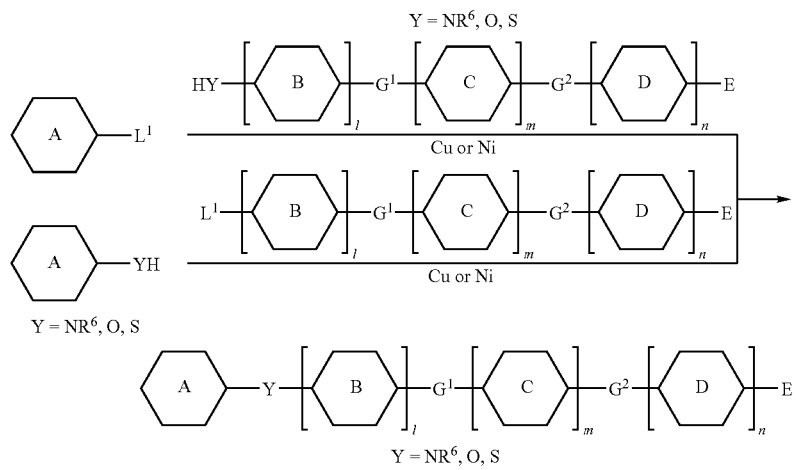

In Reaction Scheme 3, ring A, ring B, ring C, ring D, l, m, n, $G^1$, $G^2$, $R^6$ and E are the same as defined in Formula 1, and $L^1$ is the same as defined in Reaction Scheme 1.

Also, the compound represented by Formula 1 may be prepared by Reaction Scheme 4.

In Reaction Schemes 3 and 4, an aryl substitution reaction may be used to synthesize a compound in which $Y=NR^6$, O, S, etc., and an oxidation reaction may be used to introduce SO and $SO_2$.

[Reaction Scheme 4]

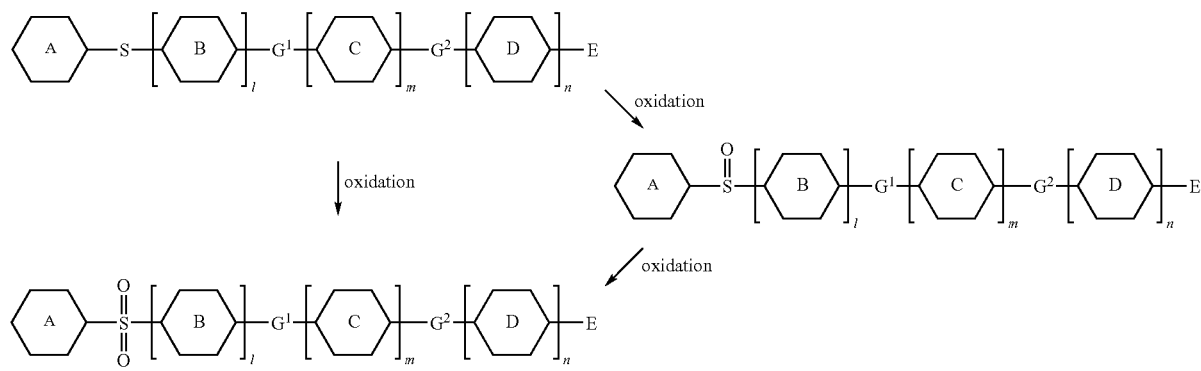

In Reaction Scheme 4, ring A, ring B, ring C, ring D, l, m, n, $G^1$, $G^2$ and E are the same as defined in Formula 1.

Also, the compound represented by Formula 1 may be prepared by Reaction Scheme 5.

[Reaction Scheme 5]

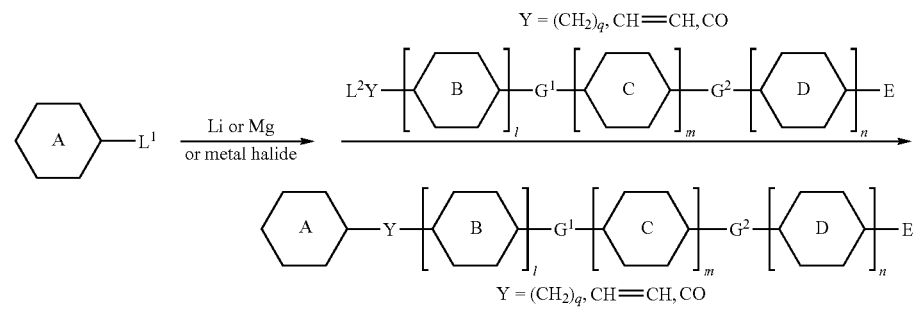

In Reaction Scheme 5, ring A, ring B, ring C, ring D, l, m, n, q, $G^1$, $G^2$ and E are the same as defined in Formula 1, each of $L^1$ and $L^2$ is the same as defined in Reaction Scheme 1, and Li or Mg represents a metal capable of forming anions, such as Li, n-BuLi, Mg, etc.

As described in Reaction Scheme 5, through a nucleophilic substitution reaction, a compound in which $Y=(CH_2)_q$, CH=CH, CO may be prepared.

Also, the compound represented by Formula 1 may be prepared by Reaction Scheme 6.

MsCl, TsCl, EDC, DCC, etc. may be used to prepare an ester compound, or Dean-Stark may be used to carry out an esterification reaction.

In the method of preparing the compound represented by Formula 1 according to the present invention, any reactant capable of showing the same or similar effects to that of the reactant used in Reaction Schemes 1 to 7 may be used, and any preparation method having a similar scheme to that of Reaction Schemes 1 to 7 may be employed.

[Reaction Scheme 6]

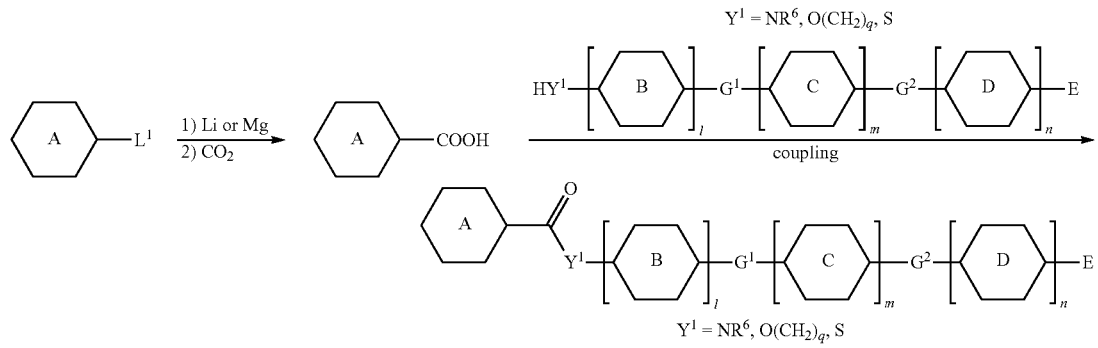

In Reaction Scheme 6, ring A, ring B, ring C, ring D, l, m, n, q, $G^1$, $G^2$, $R^6$ and E are the same as defined in Formula 1, $L^1$ is the same as defined in Reaction Scheme 1, and Li or Mg represents a metal capable of forming anions, such as Li, n-BuLi, Mg, etc.

Also, the compound represented by Formula 1 may be prepared by Reaction Scheme 7.

A resin composition according to the present invention includes a polymer resin and a silicon containing compound represented by Formula 1 of the present invention. Herein, the silicon containing compound represented by Formula 1 may play a role of controlling the optical characteristic of the polymer resin.

[Reaction Scheme 7]

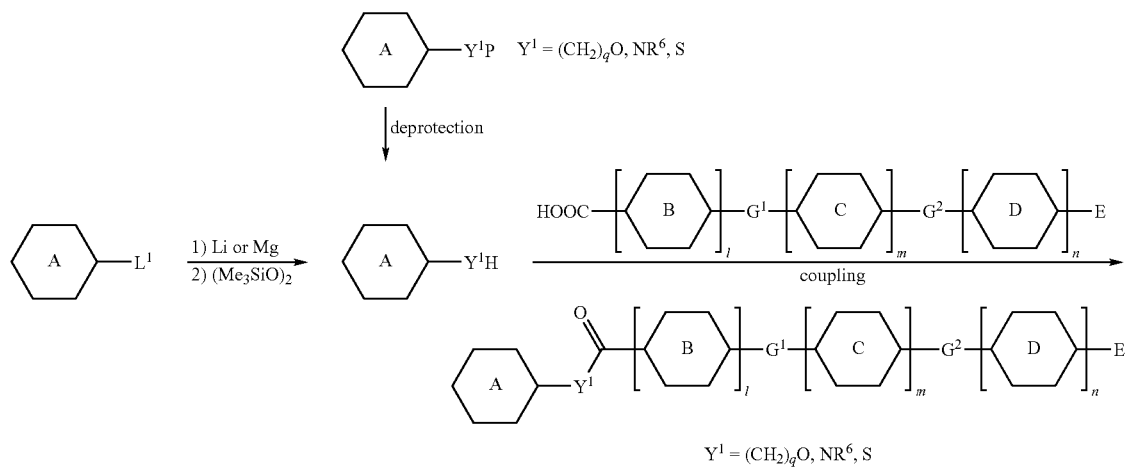

In Reaction Scheme 7, ring A, ring B, ring C, ring D, l, m, n, q, $G^1$, $G^2$, $R^6$ and E are the same as defined in Formula 1, $L^1$ is the same as defined in Reaction Scheme 1, Li or Mg represents a metal capable of forming anions, such as Li, n-BuLi, Mg, etc., and P represents a protection group.

Based on Reaction Schemes 6 and 7, a $CO_2H$ group may be prepared by bubbling $CO_2$ gas, and an OH group may be introduced by using $(Me_3SiO)_2$. Herein, $SOCl_2$, $COCl_2$, When used for such a purpose, the silicon containing compound represented by Formula 1 may be used alone or in combination. Also, within the resin composition, the polymer resin and the anisotropic compound represented by Formula 1 may be used in a weight ratio of 50:50 to 99:1, preferably of 70:30 to 99:1, and more preferably of 80:20 to 99:1.

As the polymer resin, which can be mixed with the compound represented by Formula 1, a conventional polymer resin for optical use may be used with no particular limitation.

Examples of the polymer resin include polyimide, polyamide imide, polyamide, polyetherimide, polyetheretherketone, polyetherketone, polyketone sulfide, polyethersulfone, cycloolefin polymer, polysulfone, polyphenylene sulfide, polyphenylene oxide, polyethylene terephthalate, polybutylene terephthalate, polyethylene naphthalate, polyacetal, polycarbonate, polyacrylate, acrylic resin, polyvinyl alcohol, polypropylene, cellulose, triacetyl cellulose, epoxy resin, phenol resin, etc., but the present invention is not limited thereto. Also, the polymer resins may be used alone or in combination, and herein, the use amount is not particularly limited.

Also, the resin composition according to the present invention may include an organic solvent as required, in addition to the polymer resin, and the anisotropic compound. The organic solvent included in the composition facilitates the application (coating) of the resin composition of the present invention on a substrate.

Herein, as the organic solvent, conventional organic solvents known in the art may be used without any particular limitation. Non-limiting examples of the organic solvent include: hydrocarbons such as cyclohexane, cyclopentane, benzene, toluene, xylene, butylbenzene, etc.; ketones such as acetone, methyl ethyl ketone, methyl isobutyl ketone, cyclohexanone, etc.; esters such as ethyl acetate, ethylene glycol monomethyl ether acetate, propylene glycol monomethyl ether acetate, gamma-butyrolactone, etc.; amides such as 2-pyrrolidone, N-methyl-2-pyrrolidone, dimethylformamide, dimethylacetamide, etc.; halogens such as chloroform, dichloromethane, carbon tetrachloride, dichloroethane, tetrachloroethane, tetrachloroethylene, chlorobenzene, etc.; alcohols such as t-butyl alcohol, diacetone alcohol, glycerin, monoacetin, ethylene glycol, triethylene glycol, hexylene glycol, ethylene glycol monomethyl ether, etc.; phenols such as phenol, parachlorophenol, etc.; and ethers such as methoxybenzene, 1,2-dimethoxybenzene, diethylene glycol dimethyl ether, ethylene glycol dimethyl ether, ethylene glycol diethyl ether, propylene glycol dimethyl ether, propylene glycol diethyl ether, diethylene glycol dimethyl ether, diethylene glycol diethyl ether, dipropylene glycol dimethyl ether, dipropylene glycol diethyl ether, etc. Also, the organic solvents may be used alone or in combination, and herein, the use amount is not particularly limited.

Also, the resin composition of the present invention may include a surfactant as required. A surfactant may be used to allow the composition to be easily applied on a substrate. As the surfactant, conventional surfactants known in the art may be used without any particular limitation, and the addition amount may vary according to the kind of surfactant, the composition ratio of components of a mixture, the kind of solvent, and the kind of substrate.

Also, the resin composition of the present invention may include a stress reducing agent, a leveling agent, etc. as an additional additive.

An optical member according to the present invention includes the resin composition of the present invention.

Herein, when a film-type optical member is obtained by using the resin composition of the present invention, the resin solids including the compound represented by Formula 1 are usually included in an amount of 0.1 to 90 wt %, preferably of 1 to 50 wt %, and more preferably of 5 to 40 wt %, based on the total resin composition including a solvent. If the concentration of the resin composition is less than the lower limit, it is difficult to secure the thickness of a film, and if the concentration is greater than the upper limit, it is difficult to obtain a film having a uniform thickness due to high viscosity of a solution.

Also, the film obtained by using the resin composition of the present invention may be a uniaxially oriented film or a biaxially oriented film, and the polymer film may be used after surface treatment, such as hydrophilic treatment or hydrophobic treatment, and may be a laminated film or glass.

Also, the film may be made into a transparent film by using the resin composition of the present invention, and a melt-molding method or a solvent cast method, etc. In manufacturing the transparent film by the solvent cast method, the resin composition is applied on a support, such as a metal drum, a still belt, a polyester film, Teflon, etc., a solvent is dried in a drying furnace by using a roller, and then a film is peeled from the support. The amount of residual solvent in the transparent film is usually 10 wt % or less, preferably 5 wt % or less, and more preferably 1 wt % or less. If the amount of residual solvent is greater than the upper limit, the heat resistance of the film shows a tendency to be decreased. The manufactured transparent film may control the optical characteristic of the polymer resin by uniaxial orienting or biaxial orienting.

Reference will now be made in detail to the preferred embodiments of the present invention. However, the following examples are illustrative only, and the scope of the present invention is not limited thereto.

Example 1

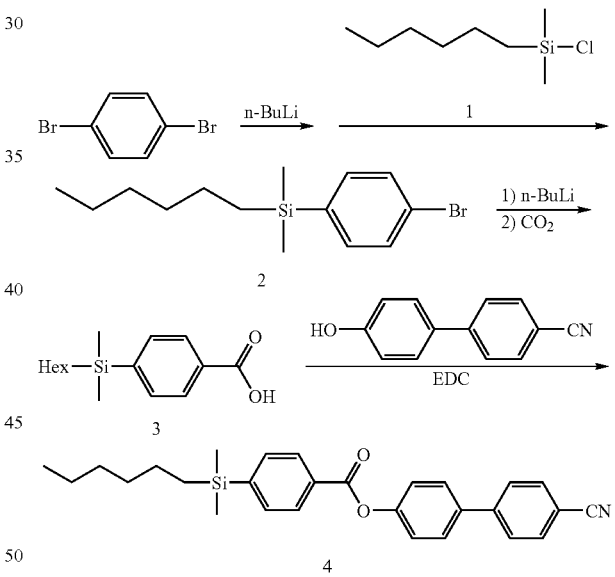

1,4-Dibromobenzene was dissolved in an anhydrous THF solvent, and 1.0 equivalent of n-BuLi was gradually added at −78° C., followed by stirring at low temperatures for about 2 hours to generate anions. Then, 1.05 equivalents of a compound 1 was dropwise added thereto. After the completion of the addition, the temperature was gradually raised up to room temperature, followed by stirring at room temperature for about 2 hours. After the completion of the reaction, the mixture was worked up with hexane and water, and purified via silica gel to obtain a compound 2 at a yield of 95%.

The compound 2 was dissolved in an anhydrous THF solvent, and 1.05 equivalents of n-BuLi was gradually added at −78° C., followed by stirring at low temperatures for about 2 hours to generate anions. Then, excess $CO_2$ was bubbled, and after the completion of the reaction, 10% HCl was used to adjust pH to about 3. The mixture was worked up with ether and water, and purified via silica gel to obtain a compound 3 at a yield of 80%.

The compound 3 and 4-cyano-4'-hydroxybiphenyl were dissolved in $CH_2Cl_2$, and 1.1 equivalents of EDC and 0.1 equivalents of DMAP were added thereto, followed by stirring at room temperature for about 10 hours. After the completion of the reaction, the mixture was worked up with $CH_2Cl_2$, and recrystallized in hexane to obtain a final compound 4 at a yield of 85% or more. $^1$HNMR of the compound 4 is as follows.

$^1$HNMR (400 MHz, $CDCl_3$): δ 0.30 (s, 6H), 0.69~0.81 (m, 2H), 0.85~0.93 (m, 3H), 1.20~1.39 (m, 8H), 7.62 (d, 2H), 7.35 (d, 2H), 7.67 (d, 2H), 7.70 (d, 2H), 7.74 (d, 2H), 8.17 (d, 2H).

Example 2

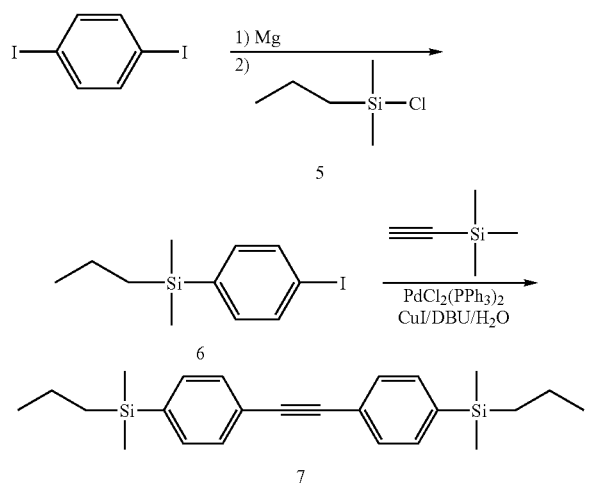

1,4-Dibromobenzene was dissolved in an anhydrous THF solvent, and 1.0 equivalent of n-BuLi was gradually added at −78° C., followed by stirring at low temperatures for about 2 hours to generate anions. Then, 1.05 equivalents of a compound 5 was dropwise added thereto. After the completion of the addition, the temperature was gradually raised up to room temperature, followed by stirring at room temperature for about 2 hours. After the completion of the reaction, the mixture was worked up with hexane and water, and purified via silica gel to obtain a compound 6 at a yield of 92%.

The compound 6 was dissolved in benzene, and 0.1 equivalents of CuI, 0.03 equivalents of $PdCl_2(PPh_3)_2$, 5.0 equivalents of DBU, 0.5 equivalents of trimethylsilyl acetylene and 0.4 equivalents of $H_2O$ were added, followed by stirring at 60° C. for about 10 hours. After the completion of the reaction, the mixture was worked up with 10% HCl and ether, and purified via silica gel to obtain a final compound 7 at a yield of 83%. $^1$HNMR of the compound 7 is as follows.

$^1$HNMR (400 MHz, $CDCl_3$): δ 0.31 (s, 12H), 0.69~0.80 (m, 4H), 0.86~0.92 (m, 6H), 1.62~1.71 (m, 4H), 7.45~7.54 (m, 8H).

Example 3

Compatibility Test 90 parts by weight of general-purpose acrylate polymer resin (Mw=100,000), and 10 parts by weight of the compound synthesized in Example 1 were dissolved in 400 parts by weight of ethyl acetate (concentration=20 wt %), and the resultant solution was applied on glass and baked at 110° C. for 3 minutes. After storage of the resultant product at room temperature for 24 hours, whether solid was precipitated on the surface or not was observed by an optical microscope or naked eyes. FIG. 1 shows the result. According to the compatibility test result, an anisotropic compound was not precipitated, even after 24 hours.

Example 4

Compatibility Test

Figure 2:
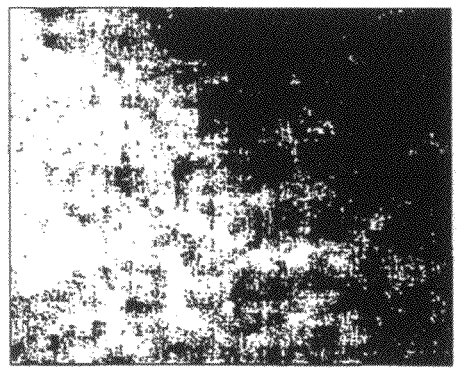

A compatibility test was carried out in the same manner as described in Example 3, except that the compound synthesized in Example 2, instead of the compound synthesized in Example 1, was used in an amount of 10 parts by weight. FIG. 2 shows the result. According to the compatibility test result, an anisotropic compound was not precipitated, even after 24 hours.

Comparative Example 1

Compatibility Test

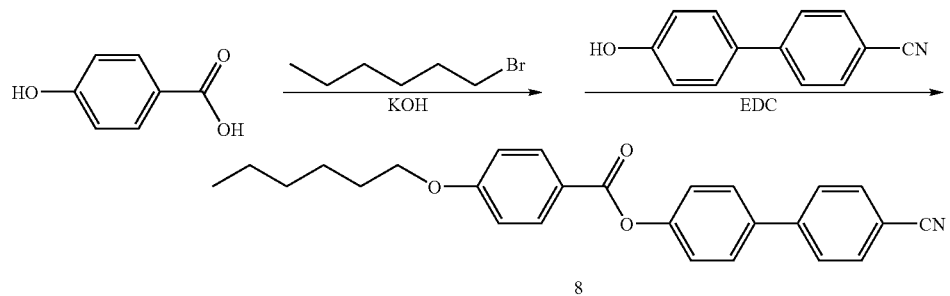

1.0 equivalent of p-Hydroxybenzoic acid was dissolved in a mixed solvent (ethanol:water=7:3), and 1.0 equivalent of bromohexane and 2.2 equivalents of KOH were added, followed by stirring at 90° C. for about 10 hours. Then, ethanol was distilled under reduced pressure, and 10% HCl(aq) was gradually added to adjust pH to 1 to 3. Then, the resultant solid was subjected to filtration and drying, and the dried resultant product, together with 1.0 equivalent of 4-cyano-4'-hydroxybiphenyl, was dissolved in $CH_2Cl_2$. 1.1 equivalents of EDC and 0.1 equivalents of DMAP were added thereto, and stirring was carried out at room temperature for about 10 hours. After the completion of the reaction, the mixture was worked up with CH$_2$Cl$_2$, and purified via silica gel to obtain a final compound 8.

Figure 3:
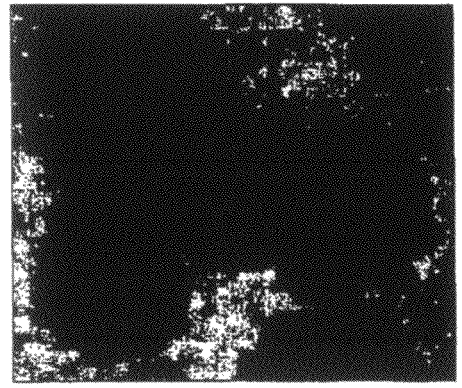
FIGS. 3 and 4 are optical microscopic photographs (×5) showing the results of the compatibility tests according to Comparative Examples 1 and 2.

A compatibility test was carried out in the same manner as described in Example 3, except that the compound 8, instead of the compound synthesized in Example 1, was used in an amount of 10 parts by weight. FIG. 3 shows the result. According to the compatibility test result, after the manufacture of a film, precipitation of the compound 8 on the surface of the film was observed at room temperature.

Comparative Example 2

Compatibility Test

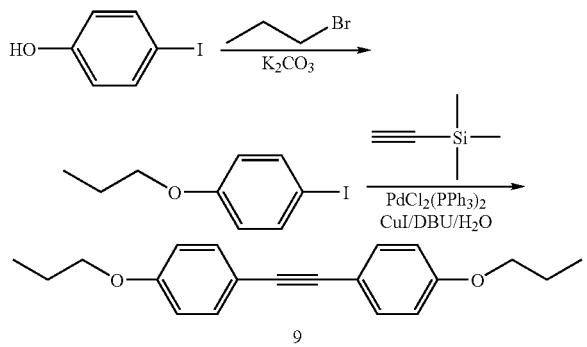

p-Iodophenol and Bromopropane (with the same equivalents) were dissolved in 1,4-dioxane, and was subjected to an alkylation reaction by K$_2$CO$_3$ base. Then, a compound 9 was prepared by a Pd coupling reaction of Example 2.

Figure 4:
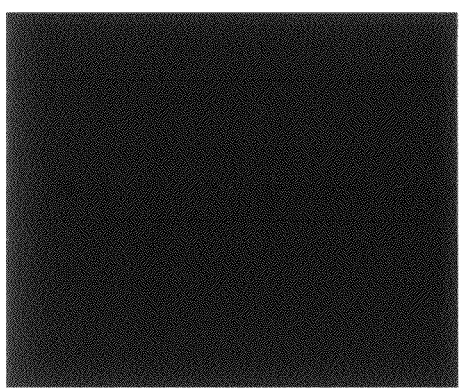

A compatibility test was carried out in the same manner as described in Example 3, except that the compound 9, instead of the compound synthesized in Example 1, was used in an amount of 10 parts by weight. FIG. 4 shows the result. According to the compatibility test result, after the manufacture of a film, precipitation of the compound 9 on the surface of the film was observed at room temperature.

Based on the results obtained from Examples 3 and 4, and Comparative Examples 1 and 2, it was determined that anisotropic silicon compounds represented by Formula 1 have high compatibility with a polymer resin.

The invention claimed is:

1. A silicon containing compound represented by Formula 1:

[Formula 1]

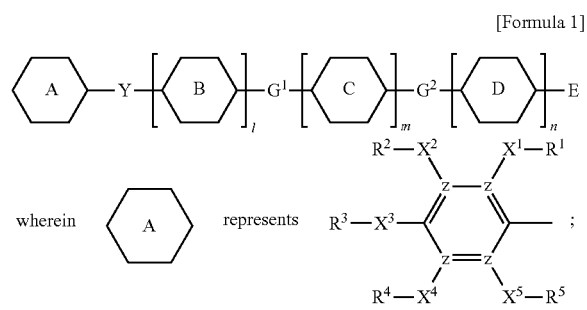

wherein A represents

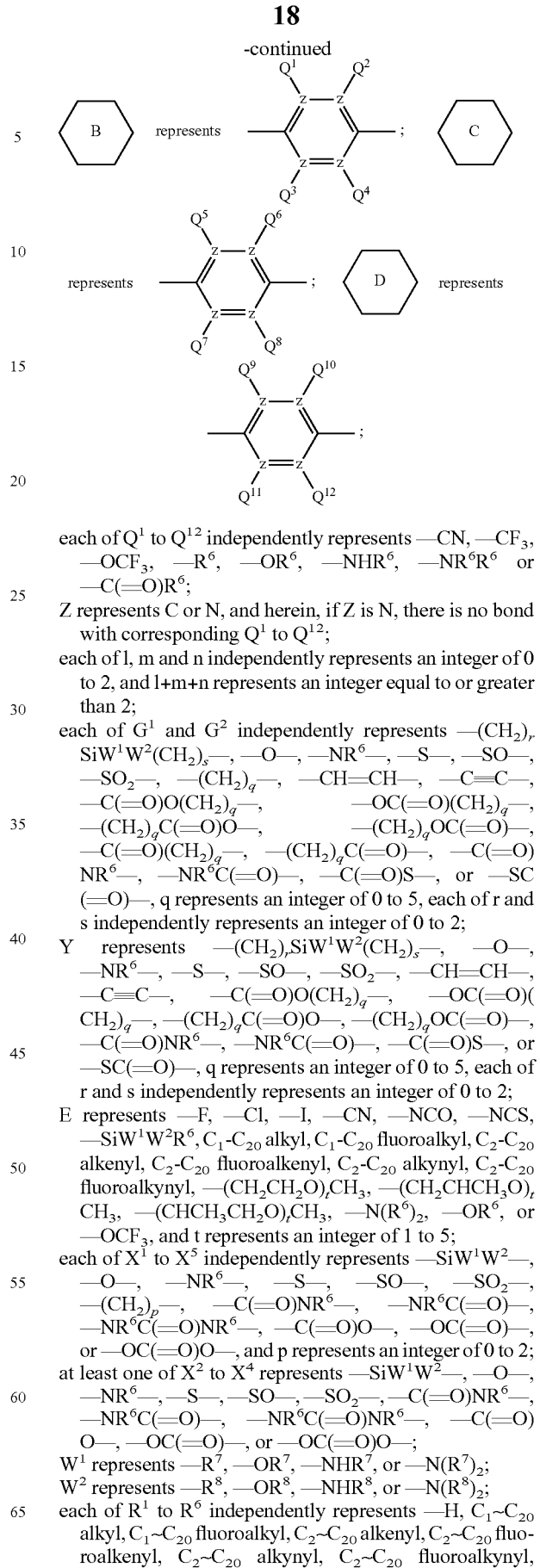

each of $Q^1$ to $Q^{12}$ independently represents —CN, —CF$_3$, —OCF$_3$, —R$^6$, —OR$^6$, —NHR$^6$, —NR$^6$R$^6$ or —C(=O)R$^6$;

Z represents C or N, and herein, if Z is N, there is no bond with corresponding $Q^1$ to $Q^{12}$;

each of l, m and n independently represents an integer of 0 to 2, and l+m+n represents an integer equal to or greater than 2;

each of G$^1$ and G$^2$ independently represents —(CH$_2$)$_r$SiW$^1$W$^2$(CH$_2$)$_s$—, —O—, —NR$^6$—, —S—, —SO—, —SO$_2$—, —(CH$_2$)$_q$—, —CH=CH—, —C≡C—, —C(=O)O(CH$_2$)$_q$—, —OC(=O)(CH$_2$)$_q$—, —(CH$_2$)$_q$C(=O)O—, —(CH$_2$)$_q$OC(=O)—, —C(=O)(CH$_2$)$_q$—, —(CH$_2$)$_q$C(=O)—, —C(=O)NR$^6$—, —NR$^6$C(=O)—, —C(=O)S—, or —SC(=O)—, q represents an integer of 0 to 5, each of r and s independently represents an integer of 0 to 2;

Y represents —(CH$_2$)$_r$SiW$^1$W$^2$(CH$_2$)$_s$—, —O—, —NR$^6$—, —S—, —SO—, —SO$_2$—, —CH=CH—, —C≡C—, —C(=O)O(CH$_2$)$_q$—, —OC(=O)(CH$_2$)$_q$—, —(CH$_2$)$_q$C(=O)O—, —(CH$_2$)$_q$OC(=O)—, —C(=O)NR$^6$—, —NR$^6$C(=O)—, —C(=O)S—, or —SC(=O)—, q represents an integer of 0 to 5, each of r and s independently represents an integer of 0 to 2;

E represents —F, —Cl, —I, —CN, —NCO, —NCS, —SiW$^1$W$^2$R$^6$, C$_1$-C$_{20}$ alkyl, C$_1$-C$_{20}$ fluoroalkyl, C$_2$-C$_{20}$ alkenyl, C$_2$-C$_{20}$ fluoroalkenyl, C$_2$-C$_{20}$ alkynyl, C$_2$-C$_{20}$ fluoroalkynyl, —(CH$_2$CH$_2$O)$_t$CH$_3$, —(CH$_2$CHCH$_3$O)$_t$CH$_3$, —(CHCH$_3$CH$_2$O)$_t$CH$_3$, —N(R$^6$)$_2$, —OR$^6$, or —OCF$_3$, and t represents an integer of 1 to 5;

each of X$^1$ to X$^5$ independently represents —SiW$^1$W$^2$—, —O—, —NR$^6$—, —S—, —SO—, —SO$_2$—, —(CH$_2$)$_p$—, —C(=O)NR$^6$—, —NR$^6$C(=O)—, —NR$^6$C(=O)NR$^6$—, —C(=O)O—, —OC(=O)—, or —OC(=O)O—, and p represents an integer of 0 to 2;

at least one of X$^2$ to X$^4$ represents —SiW$^1$W$^2$—, —O—, —NR$^6$—, —S—, —SO—, —SO$_2$—, —C(=O)NR$^6$—, —NR$^6$C(=O)—, —NR$^6$C(=O)NR$^6$—, —C(=O)O—, —OC(=O)—, or —OC(=O)O—;

W$^1$ represents —R$^7$, —OR$^7$, —NHR$^7$, or —N(R$^7$)$_2$;

W$^2$ represents —R$^8$, —OR$^8$, —NHR$^8$, or —N(R$^8$)$_2$;

each of R$^1$ to R$^6$ independently represents —H, C$_1$-C$_{20}$ alkyl, C$_1$-C$_{20}$ fluoroalkyl, C$_2$-C$_{20}$ alkenyl, C$_2$-C$_{20}$ fluoroalkenyl, C$_2$-C$_{20}$ alkynyl, C$_2$-C$_{20}$ fluoroalkynyl, —$(CH_2CH_2O)_tCH_3$, —$(CH_2CHCH_3O)_tCH_3$, or —$(CHCH_3CH_2O)_tCH_3$, and t represents an integer of 1 to 5;

each of $R^7$ to $R^8$ independently represents $C_1$~$C_{20}$ alkyl, $C_1$~$C_{20}$ fluoroalkyl, $C_2$~$C_{20}$ alkenyl, $C_2$~$C_{20}$ fluoroalkenyl, $C_2$~$C_{20}$ alkynyl, $C_2$~$C_{20}$ fluoroalkynyl, —$(CH_2CH_2O)_tCH_3$, —$(CH_2CHCH_3O)_tCH_3$, or —$(CHCH_3CH_2O)_tCH_3$, and t represents an integer of 1 to 5; and at least one of Y, $G^1$, $G^2$, E, and $X^1$ to $X^5$ is a Si containing substituent, and herein, as the Si containing substituent, in Y, $G^1$ and $G^2$, —$(CH_2)_rSiW^1W^2(CH_2)_s$— is introduced, in E, —$SiW^1W^2R^6$ is introduced, and in $X^1$ to $X^5$, —$SiW^1W^2$— is introduced.

2. The compound as claimed in claim 1, wherein l+m+n is an integer of 2 to 3.

3. The compound as claimed in claim 1, wherein refractive anisotropy is 0.2 or more.

4. The compound as claimed in claim 1, which is prepared by Reaction Scheme 2:

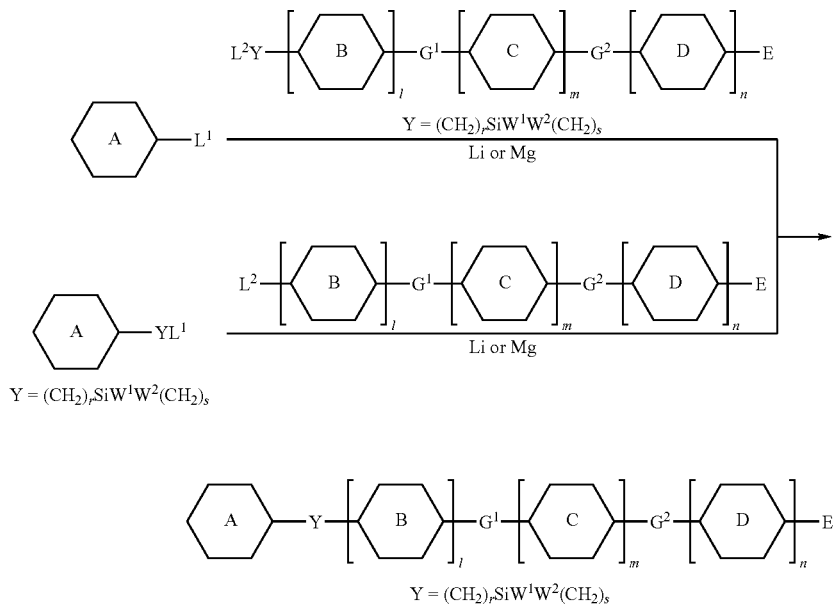

wherein ring A, ring B, ring C, ring D, l, m, n, $W^1$, $W^2$, r, s, $G^1$, $G^2$ and E are same as defined in claim 1, and each of $L^1$ and $L^2$ independently represents halide, mesylate, tosylate, or triflate.

5. The compound as claimed in claim 1, which is prepared by Reaction Scheme 3:

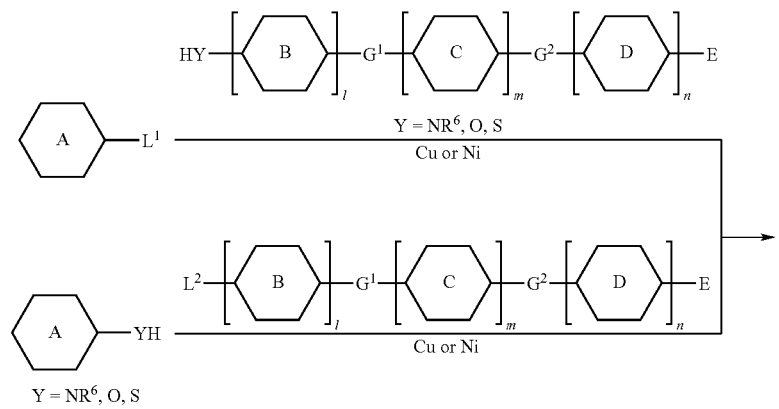

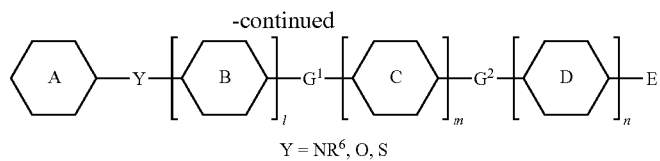

$Y = NR^6, O, S$ wherein ring A, ring B, ring C, ring D, l, m, n, $G^1$, $G^2$, $R^6$ and E are same as defined in claim 1, and $L^1$ represents halide, mesylate, tosylate, or triflate.

6. The compound as claimed in claim 1, which is prepared by Reaction Scheme 4:

[Reaction Scheme 4]

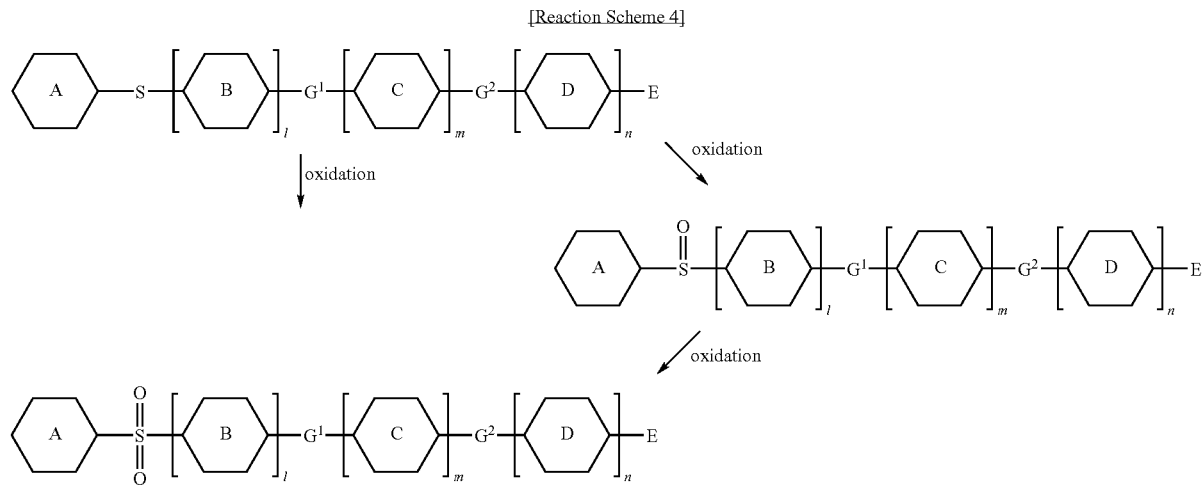

wherein ring A, ring B, ring C, ring D, l, m, n, $G^1$, $G^2$ and E are same as defined in claim 1.

7. A silicon containing compound which is represented by Formula 1 and prepared by Reaction Scheme 1:

[Formula 1]

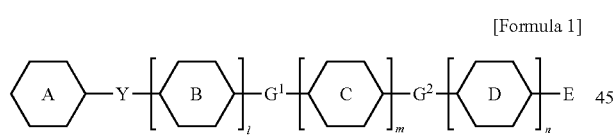

[Reaction Scheme 1]

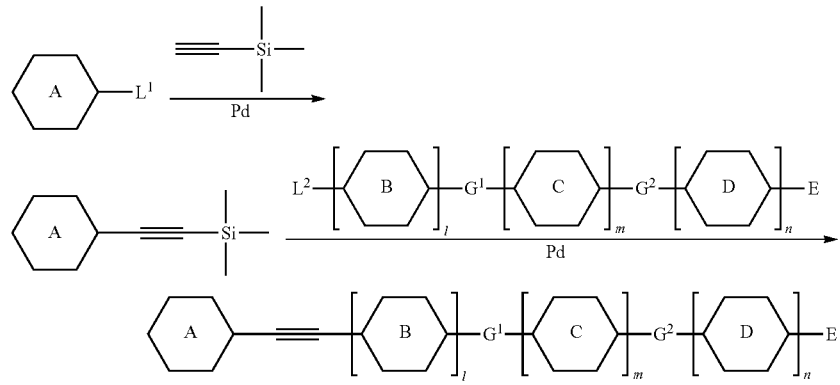

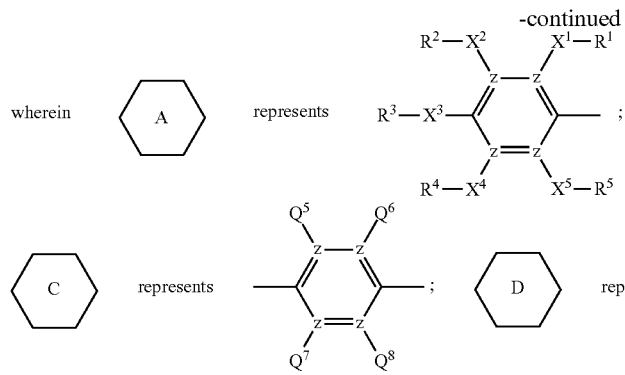
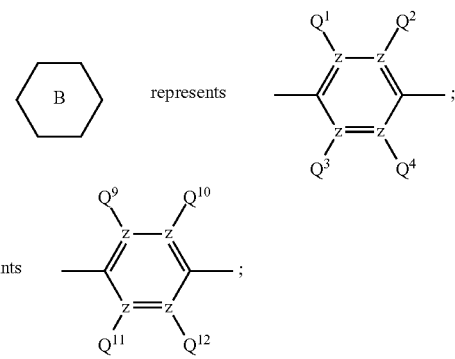

wherein ⬡A represents ... ; ⬡B represents ... ;

⬡C represents ... ; ⬡D represents ... ;

each of $Q^1$ to $Q^{12}$ independently represents —H, —CN, —$CF_3$, —$OCF_3$, —$R^6$, —$OR^6$, —$NHR^6$, —$NR^6R^6$ or —C(=O)$R^6$;

Z represents C or N, and herein, if Z is N, there is no bond with corresponding $Q^1$ to $Q^{12}$;

each of l, m and n independently represents an integer of 0 to 2, and l+m+n represents an integer equal to or greater than 2;

each of $G^1$ and $G^2$ independently represents —(CH)$_r$ $SiW^1W^2(CH_2)_s$—, —O—, —$NR^6$—, —S—, —SO—, —$SO_2$—, —(CH$_2$)$_q$—, —CH=CH—, —C≡C—, —C(=O)O(CH$_2$)$_q$—, —OC(=O)(CH$_2$)$_q$—, —(CH$_2$)$_q$C(=O)O—, —(CH$_2$)$_q$OC(=O)—, —C(=O)(CH$_2$)$_q$—, —(CH$_2$)$_q$C(=O)—, —C(=O)$NR^6$—, —$NR^6$C(=O)—, —C(=O)S—, or —SC(=O)—, q represents an integer of 0 to 5, each of r and s independently represents an integer of 0 to 2;

Y represents —C≡C—;

E represents —H, —F, —Cl, —Br, —I, —CN, —NCO, —NCS, —$SiW^1W^2R^6$, —$R^6$, —N($R^6$)$_3$, —$OR^6$, —$CF_3$, or —$OCF_3$;

each of $X^1$ to $X^5$ independently represents —$SiW^1W^2$—, —O—, —$NR^6$—, —S—, —SO—, —$SO_2$—, —(CH$_2$)$_p$—, —C(=O)$NR^6$—, —$NR^6$C(=O)—, —$NR^6$C(=O)$NR^6$—, —C(=O)O—, —OC(=O)—, or —OC(=O)O—, and p represents an integer of 0 to 2;

$W^1$ represents —$R^7$, —$OR^7$, —$NHR^7$, or —N($R^7$)$_2$;

$W^2$ represents —$R^8$, —$OR^8$, —$NHR^8$, or —N($R^8$)$_2$;

each of $R^1$ to $R^6$ independently represents —H, $C_1$~$C_{20}$ alkyl, $C_1$~$C_{20}$ fluoroalkyl, $C_2$~$C_{20}$ alkenyl, $C_2$~$C_{20}$ fluoroalkenyl, $C_2$~$C_{20}$ alkynyl, $C_2$~$C_{20}$ fluoroalkynyl, —(CH$_2$CH$_2$O)$_t$CH$_3$, —(CH$_2$CHCH$_3$O)$_t$CH$_3$, or —(CHCH$_3$CH$_2$O)$_t$CH$_3$, and t represents an integer of 1 to 5;

each of $R^7$ to $R^8$ independently represents $C_1$~$C_{20}$ alkyl, $C_1$~$C_{20}$ fluoroalkyl, $C_2$~$C_{20}$ alkenyl, $C_2$~$C_{20}$ fluoroalkenyl, $C_2$~$C_{20}$ alkynyl, $C_2$~$C_{20}$ fluoroalkynyl, —(CH$_2$CH$_2$O)$_t$CH$_3$, —(CH$_2$CHCH$_3$O)$_t$CH$_3$, or —(CHCH$_3$CH$_2$O)$_t$CH$_3$, and t represents an integer of 1 to 5; and at least one of $G^1$, $G^2$, E, and $X^1$ to $X^5$ is a Si containing substituent, and herein, as the Si containing substituent, in $G^1$ and $G^2$, —(CH$_2$)$_r$SiW$^1$W$^2$(CH$_2$)$_s$— is introduced, in E, —SiW$^1$W$^2$R$^6$ is introduced, and in $X^1$ to $X^5$, —SiW$^1$W$^2$— is introduced; and each of $L^1$ and $L^2$ independently represents halide, mesylate, tosylate, or triflate.

8. A silicon containing compound which is represented by Formula 1 and prepared by Reaction Scheme 5:

[Formula 1]

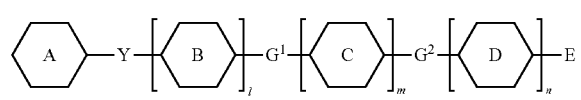

[Reaction Scheme 5]

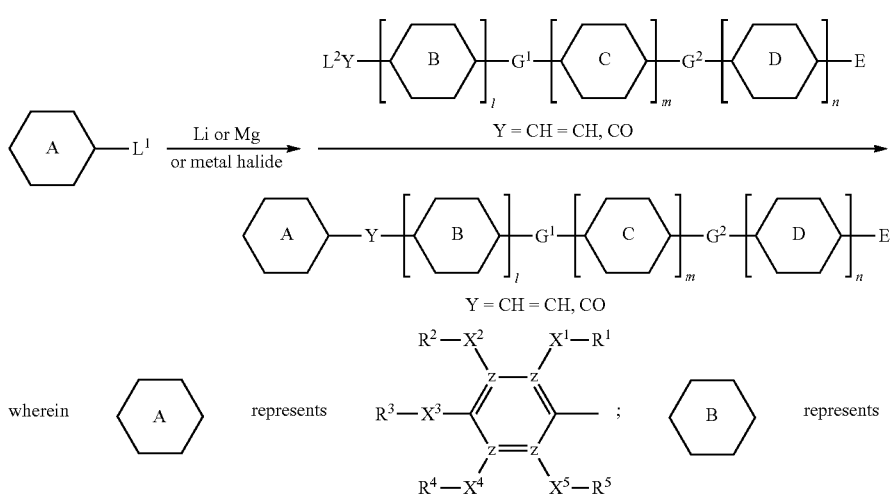

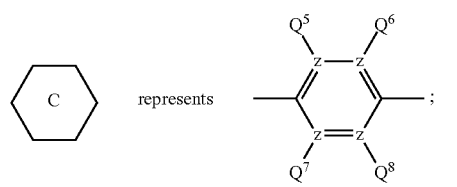 represents 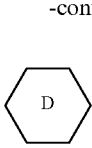 ; 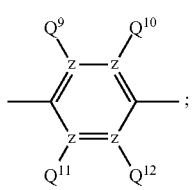 represents 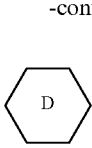 ;

each of $Q^1$ to $Q^{12}$ independently represents —H, —CN, —$CF_3$, —$OCF_3$, —$R^6$, —$OR^6$, —$NHR^6$, $NR^6R^6$ or —C(=O)$R^6$;

Z represents C or N, and herein, if Z is N, there is no bond with corresponding to $Q^{12}$;

each of l, m and n independently represents an integer of 0 to 2, and l+m+n represents an integer equal to or greater than 2;

each of $G^1$ and $G^2$ independently represents —$(CH_2)_r$ $SiW^1W^2(CH_2)_s$—, —O—, —$NR^6$—, —S—, —SO—, —$SO_2$—, —$(CH_2)_q$—, —CH=CH—, —C≡C—, —C(=O)O$(CH_2)_q$—, —OC(=O)$(CH_2)_q$—, —$(CH_2)_q$C(=O)O—, —$(CH_2)_q$OC(=O)—, —C(=O)$(CH_2)_q$—, —$(CH_2)_q$C(=O)—, —C(=O)$NR^6$—, —$NR^6$C(=O)—, —C(=O)S—, or —SC(=O)—, q represents an integer of 0 to 5, each of r and s independently represents an integer of 0 to 2;

Y represents —CH=CH—, or —CO—;

E represents —H, —F, —Cl, —Br, —I, —CN, —NCO, —NCS, —$SiW^1W^2R^6$, —$R^6$, —$N(R^6)_2$, —$OR^6$, —$CF_3$, or —$OCF_3$;

each of $X^1$ to $X^5$ independently represents —$SiW^1W^2$—, —O—, —$NR^6$—, —S—, —SO—, —$SO_2$—, —$(CH_2)_p$—, —C(=O)$NR^6$—, —$NR^6$C(=O)—, —$NR^6$C(=O)$NR^6$—, —C(=O)O—, —OC(=O)—, or —OC(=O)O—, and p represents an integer of 0 to 2;

$W^1$ represents —$R^7$, —$OR^7$, —$NHR^7$, or —$N(R^7)_2$;
$W^2$ represents —$R^8$, —$OR^8$, —$NHR^8$, or —$N(R^8)_2$;

each of $R^1$ to $R^6$ independently represents —H, $C_2$~$C_{20}$ alkyl, $C_2$~$C_{20}$ fluoroalkyl, $C_2$~$C_{20}$ alkenyl, $C_2$~$C_{20}$ fluoroalkyl, $C_2$~$C_{20}$ alkynyl, $C_2$~$C_{20}$ fluoroalkyl, —$(CH_2CH_2O)_tCH_3$, —$(CH_2CHCH_3O)_tCH_3$, or —$(CHCH_3CH_2O)_tCH_3$, and t represents an integer of 1 to 5;

each of $R^7$ to $R^8$ independently represents $C_1$~$C_{20}$ alkyl, $C_1$~$C_{20}$ fluoroalkyl, $C_2$~$C_{20}$ alkenyl, $C_2$~$C_{20}$ fluoroalkenyl, $C_2$~$C_{20}$ alkynyl, $C_2$~$C_{20}$ fluoroalkynyl, —$(CH_2CH_2O)_tCH_3$, —$(CH_2CHCH_3O)_tCH_3$, or —$(CHCH_3CH_2O)_tCH_3$, and t represents an integer of 1 to 5; and at least one of $G^1$, $G^2$, E, and $X^1$ to $X^5$ is a Si containing substituent, and herein, as the Si containing substituent, in $G^1$ and $G^2$, —$(CH_2SiW^1W^2(CH_2)_s$— is introduced, in E, —$SiW^1W^2R^6$ is introduced, and in $X^1$ to $X^5$, —$SiW^1W^2$— is introduced; and each of $L^1$ and $L^2$ independently represents halide, mesylate, tosylate, or triflate.

9. A silicon containing compound which is represented by Formula 1 and prepared by Reaction Scheme 6:

[Formula 1]

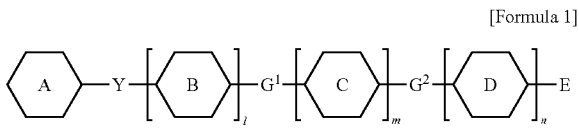

[Reaction Scheme 6]

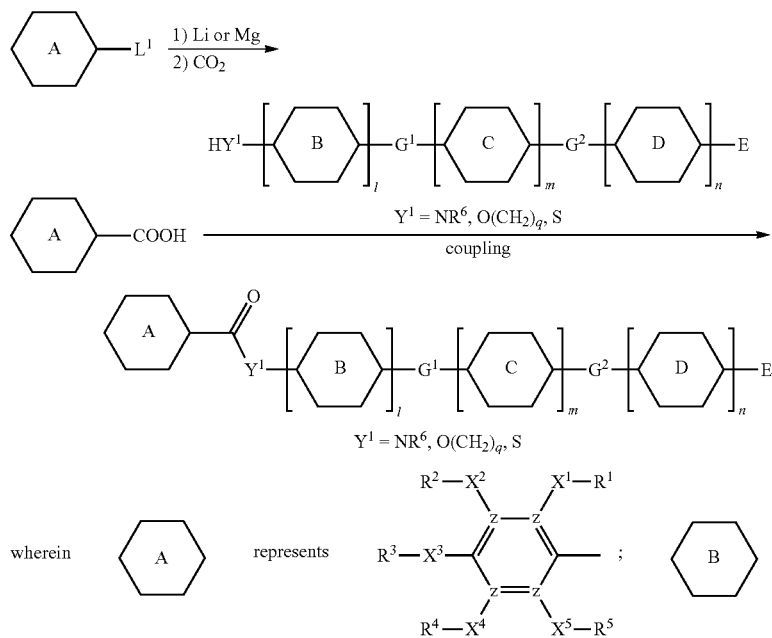

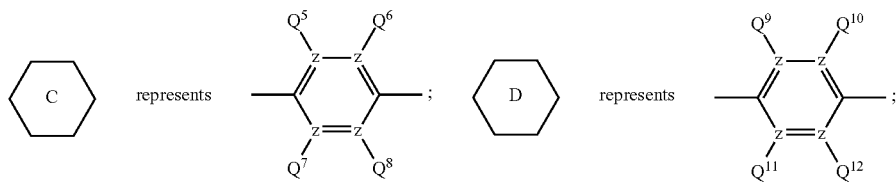

each of Q$^1$ to Q$^{12}$ independently represents —H, —CN, —CF$_3$, —OCF$_3$, —R$^6$, —OR$^6$, —NHR$^6$, —NR$^6$R$^6$ or —C(=O)R$^6$;

Z represents C or N, and herein, if Z is N, there is no bond with corresponding Q$^1$ to Q$^{12}$;

each of l, m and n independently represents an integer of 0 to 2, and l+m+n represents an integer equal to or greater than 2;

each of G$^1$ and G$^2$ independently represents —(CH$_2$)$_r$ SiW$^1$W$^2$(CH$_2$)$_s$—, —O—, —NR$^6$—, —S—, —SO—, —SO$_2$—, —(CH$_2$)$_q$—, —CH=CH—, —C≡C—, —C(=O)O(CH$_2$)$_q$—, —OC(=O)(CH$_2$)$_q$—, —(CH$_2$)$_q$C(=O)O—, —(CH$_2$)$_q$OC(=O)—, —C(=O)(CH$_2$)$_q$—, —(CH$_2$)$_q$C(=O)—, —C(=O)NR$^6$—, —NR$^6$C(=O)—, —C(=O)S—, or —SC(=O)—, q represents an integer of 0 to 5, each of r and s independently represents an integer of 0 to 2;

Y represents —C(=O) Y$^1$—;

Y$^1$ represents —NR$^6$—, —O(CH$_2$)$_q$—, or —S—, and q represents an integer of 0 to 5;

E represents —H, —F, —Cl, —Br, —I, —CN, —NCO, —NCS, —SiW$^1$W$^2$R$^6$, —R$^6$, —N(R$^6$)$_2$, —OR$^6$, —CF$_3$, or —OCF$_3$;

each of X$^1$ to X$^5$ independently represents —SiW$^1$W$^2$—, —O—, —NR$^6$—, —S—, —SO—, —SO$_2$—, —(CH$_2$)$_p$—, —C(=O)NR$^6$—, —NR$^6$C(=O)—, —NR$^6$C(=O)NR$^6$—, —C(=O)O—, —OC(=O)—, or —OC(=O)O—, and p represents an integer of 0 to 2;

W$^1$ represents —R$^7$, —OR$^7$, —NHR$^7$, or —N(R$^7$)$_2$;

W$^2$ represents —R$^8$, —OR$^8$, —NHR$^8$, or —N(R$^8$)$_2$;

each of R$^1$ to R$^6$ independently represents —H, C$_1$~C$_{20}$ alkyl, C$_1$~C$_{20}$ fluoroalkyl, C$_2$~C$_{20}$ alkenyl, C$_1$~C$_{20}$ fluoroalkenyl, C$_2$~C$_{20}$ alkynyl, C$_2$~C$_{20}$ fluoroalkynyl, —(CH$_2$~CH$_2$O)$_t$CH$_3$, —(CH$_2$CHCH$_3$O)$_t$CH$_3$, or —(CHCH$_3$CH$_2$O)$_t$CH$_3$, and t represents an integer of 1 to 5;

each of R$^7$ to R$^8$ independently represents C$_1$~C$_{20}$ alkyl, C$_1$~C$_{20}$ fluoroalkyl, C$_2$~C$_{20}$ alkenyl, C$_2$~C$_{20}$ fluoroalkenyl, C$_2$~C$_{20}$ alkynyl, C$_2$~C$_{20}$ fluoroalkynyl, —(CH$_2$CHO)$_t$CH$_3$, —(CH$_2$CHCH$_3$O)$_t$CH$_3$, or —(CHCH$_3$CH$_2$O)$_t$CH$_3$, and t represents an integer of 1 to 5; and at least one of G$^1$, G$^2$, E, and X$^1$ to X$^5$ is a Si containing substituent, and herein, as the Si containing substituent, in G$^1$ and G$^2$, —(CH$_2$)$_r$SiW$^1$W$^2$(CH$_2$)$_s$— is introduced, in E, —SiW$^1$W$^2$R$^6$ is introduced, and in X$^1$ to X$^5$, —SiW$^1$W$^2$— is introduced; and L$^1$ represents halide, mesylate, tosylate, or triflate.

10. A silicon containing compound which is represented by Formula 1 and prepared by Reaction Scheme 7:

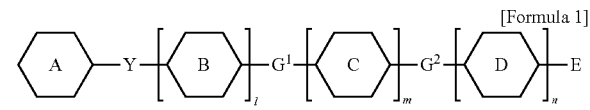

[Formula 1]

[Reaction Scheme 7]

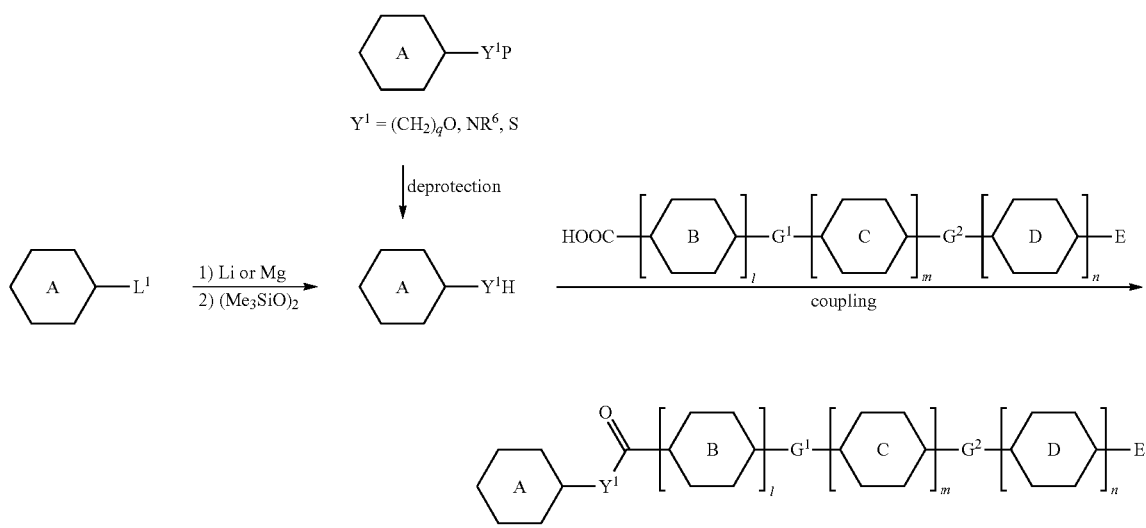

-continued

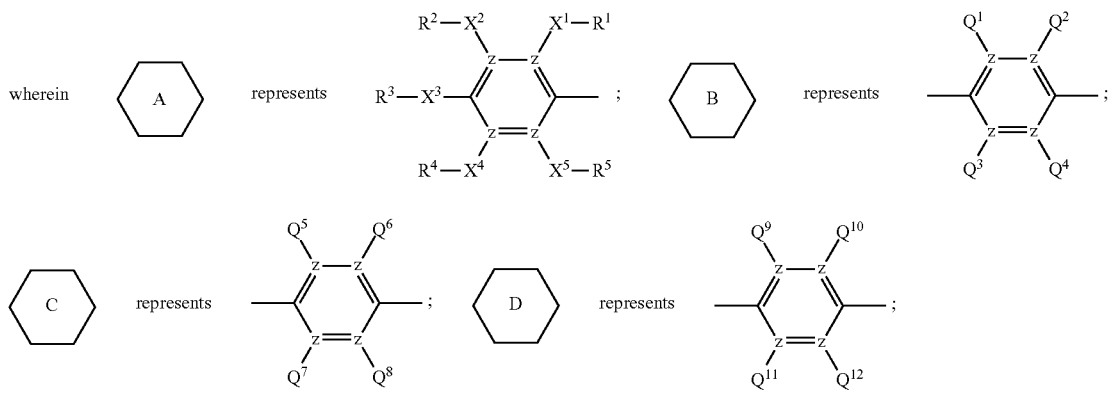

each of $Q^1$ to $Q^{12}$ independently represents —H, —CN, —CF$_3$, —OCF$_3$, —R$^6$, —OR$^6$, —NHR$^6$, —NR$^6$R$^6$ or —C(=O)R$^6$, Z represents C or N, and herein, if Z is N, there is no bond with corresponding $Q^1$ to $Q^{12}$;

each of l, m and n independently represents an integer of 0 to 2, and l+m+n represents an integer equal to or greater than 2;

each of $G^1$ and $G^2$ independently represents —(CH$_2$)$_r$SiW$^1$W$^2$(CH$_2$)$_s$—, —O—, —NR$^6$—, —S—, —SO—, —SO$_2$—, —(CH$_2$)$_q$—, —CH=CH—, —C≡C—, —C(=O)O(CH$_2$)$_q$—, —OC(=O)(CH$_2$)$_q$—, —(CH$_2$)C(=O)O—, —(CH$_2$)$_q$OC(=O)—, —C(=O)(CH$_2$)$_q$—, —(CH$_2$)$_q$C(=O)—, —C(=O)NR$^6$—, —NR$^6$C(=O)—, —C(=O)S—, or —SC(=O)—, q represents an integer of 0 to 5, each of r and s independently represents an integer of 0 to 2;

Y represents —Y$^1$C(=O)—;

$Y^1$ represents —(CH$_2$)$_q$O—, —NR$^6$—, or —S—, and q represents an integer of 0 to 5;

E represents —H, —F, —Cl, —Br, —I, —CN, —NCO, —NCS, —SiW$^1$W$^2$R$^6$, —R$^6$, —N(R$^6$)$_2$, —OR$^6$, —CF$_3$, or —OCF$_3$;

each of $X^1$ to $X^5$ independently represents —SiW$^1$W$^2$—, —O—, —NR$^6$—, —S—, —SO—, —SO$_2$—, —(CH$_2$)$_p$—, —C(=O)NR$^6$—, —NR$^6$C(=O)—, —NR$^6$C(=O)NR$^6$—, —C(=O)O—, —OC(=O)—, or —OC(=O)O—, and p represents an integer of 0 to 2;

$W^1$ represents —R$^7$, —OR$^7$, —NHR$^7$, or —N(R$^7$)$_2$;

$W^2$ represents —R$^8$, —OR$^8$, —NHR$^8$, or —N(R$^8$)$_2$;

each of $R^1$ to $R^6$ independently represents —H, C$_1$~C$_{20}$ alkyl, C$_1$~C$_{20}$ fluoroalkyl, C$_2$~C$_{20}$ alkenyl, C$_2$~C$_{20}$ fluoroalkenyl, C$_2$~C$_{20}$ alkynyl, C$_2$~C$_{20}$ fluoroalkynyl, —(CH$_2$CH$_2$O)$_t$CH$_3$, —(CH$_2$CHCH$_3$O)$_t$CH$_3$, or —(CHCH$_3$CH$_2$O)$_t$CH$_3$, and t represents an integer of 1 to 5;

each of $R^7$ to $R^8$ independently represents C$_1$~C$_{20}$ alkyl, C$_1$~C$_{20}$ fluoroalkyl, C$_1$~C$_{20}$ alkenyl, C$_2$~C$_{20}$ fluoroalkenyl, C$_2$~C$_{20}$ alkynyl, C$_2$~C$_{20}$ fluoroalkynyl, —(CH$_2$–CH$_2$O)$_t$CH$_3$, —(CH$_2$CHCH$_3$O)$_t$CH$_3$, or —(CHCH$_3$CH$_2$O)$_t$CH$_3$, and t represents an integer of 1 to 5; and at least one of $G^1$, $G^2$, E, and $X^1$ to $X^5$ is a Si containing substituent, and herein, as the Si containing substituent, in $G^1$ and $G^2$, —(CH$_2$)$_r$SiW$^1$W$^2$(CH$_2$)$_s$— is introduced, in E, —SiW$^1$W$^2$R$^6$ is introduced, and in $X^1$ to $X^5$, —SiW$^1$W$^2$— is introduced; and $L^1$ represents halide, mesylate, tosylate, or triflate, and P represents a protection group.

11. A resin composition comprising a polymer resin; and the silicon containing compound represented by Formula 1:

[Formula 1]

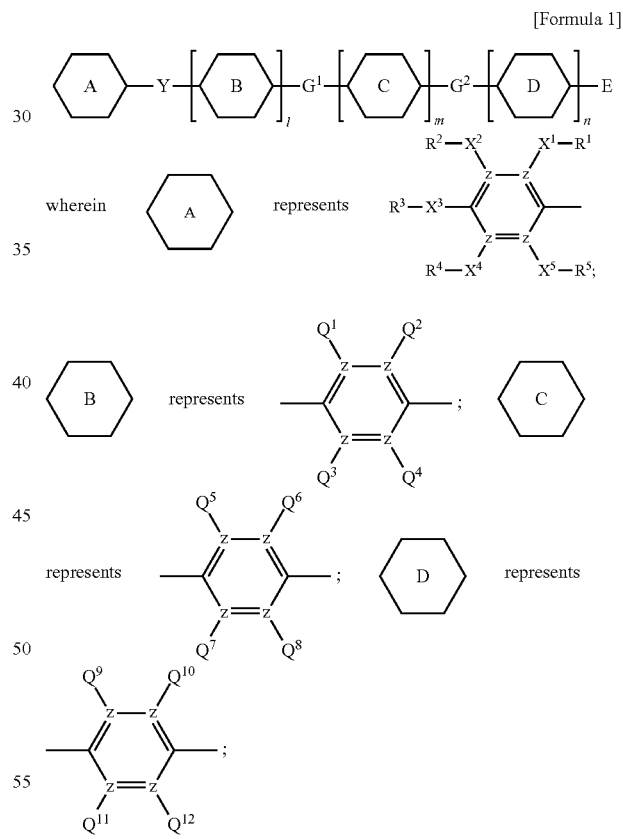

each of $Q^1$ to $Q^{12}$ independently represents —H, —CN, —CF$_3$, —OCF$_3$, —R$^6$, —OR$^6$, —NHR$^6$, —NR$^6$R$^6$ or —C(=O)R$^6$;

Z represents C or N, and herein, if Z is N, there is no bond with corresponding $Q^1$ to $Q^{12}$;

each of l, m and n independently represents an integer of 0 to 2, and l+m+n represents an integer equal to or greater than 2;

each of $G^1$ and $G^2$ independently represents —$(CH_2)_r$ $SiW^1W^2(CH_2)_s$—, —O—, —$NR^6$—, —S—, —SO—, —$SO_2$—, —$(CH_2)_q$—, —CH=CH—, —C≡C—, —C(=O)O$(CH_2)_q$—, —OC(=O)$(CH_2)_q$—, —$(CH_2)_q$C(=O)O—, —$(CH_2)_q$OC(=O)—, —C(=O)$(CH_2)_q$—, —$(CH_2)_q$C(=O)—, —C(=O)$NR^6$—, —$NR^6$C(=O)—, —C(=O)S—, or —SC(=O)—, q represents an integer of 0 to 5, each of r and s independently represents an integer of 0 to 2;

Y represents —$(CH_2)_r SiW^1W^2(CH_2)_s$—, —O—, —$NR^6$—, —S—, —SO—, —$SO_2$—, —CH=CH—, —C≡C—, —C(=O)O$(CH_2)_q$—, —OC(=O)$(CH_2)_q$—, —$(CH_2)_q$C(=O)O—, —$(CH_2)_q$OC(=O)—, —C(=O)$NR^6$—, —$NR^6$C(=O)—, —C(=O)S—, or —SC(=O)—, q represents an integer of 0 to 5, each of r and s independently represents an integer of 0 to 2;

E represents —H, —F, —Cl, —Br, —I, —CN, —NCO, —NCS, —$SiW^1W^2R^6$, —$R^6$, —$N(R^6)_2$, —$OR^6$, —$CF_3$, or —$OCF_3$;

each of $X^1$ to $X^5$ independently represents —$SiW^1W^2$—, —O—, —$NR^6$—, —S—, —SO—, —$SO_2$—, —$(CH_2)_p$—, —C(=O)$NR^6$—, —$NR^6$C(=O)—, —$NR^6$C(=O)$NR^6$—, —C(=O)O—, —OC(=O)—, or —OC(=O)O—, and p represents an integer of 0 to 2;

$W^1$ represents —$R^7$, —$OR^7$, —$NHR^7$, or —$N(R^7)_2$;
$W^2$ represents —$R^8$, —$OR^8$, —$NHR^8$, or —$N(R^8)_2$;
each of $R^1$ to $R^6$ independently represents —H, $C_1$~$C_{20}$ alkyl, $C_1$~$C_{20}$ fluoroalkyl, $C_2$~$C_{20}$ alkenyl, $C_2$~$C_{20}$ fluoroalkenyl, $C_2$~$C_{20}$ alkynyl, $C_2$~$C_{20}$ fluoroalkynyl, —$(CH_2CH_2O)_tCH_3$, —$(CH_2CHCH_3O)_tCH_3$, or —$(CHCH_3CH_2O)_tCH_3$, and t represents an integer of 1 to 5;

each of $R^7$ to $R^8$ independently represents $C_1$~$C_{20}$ alkyl, $C_1$~$C_{20}$ fluoroalkyl, $C_2$~$C_{20}$ alkenyl, $C_2$~$C_{20}$ fluoroalkenyl, $C_2$~$C_{20}$ alkynyl, $C_2$~$C_{20}$ fluoroalkynyl, —$(CH_2CH_2O)_tCH_3$, —$(CH_2CHCH_3O)_tCH_3$, or —$(CHCH_3CH_2O)_tCH_3$, and t represents an integer of 1 to 5; and at least one of Y, $G^1$, $G^2$, E, and $X^1$ to $X^5$ is a Si containing substituent, and herein, as the Si containing substituent, in Y, $G^1$ and $G^2$, —$(CH_2)_rSiW^1W^2(CH_2)$— is introduced, in E, —$SiW^1W^2R^6$ is introduced, and in $X^1$ to $X^5$, —$SiW^1W^2$— is introduced.

12. The resin composition as claimed in claim 11, wherein weight ratio of the polymer resin: the compound represented by Formula 1 is 50:50 to 99:1.

13. An optical member comprising the resin composition as claimed in claim 11.

14. The resin composition as claimed in claim 11, wherein the compound is prepared by Reaction Scheme 1:

[Reaction Scheme 1]

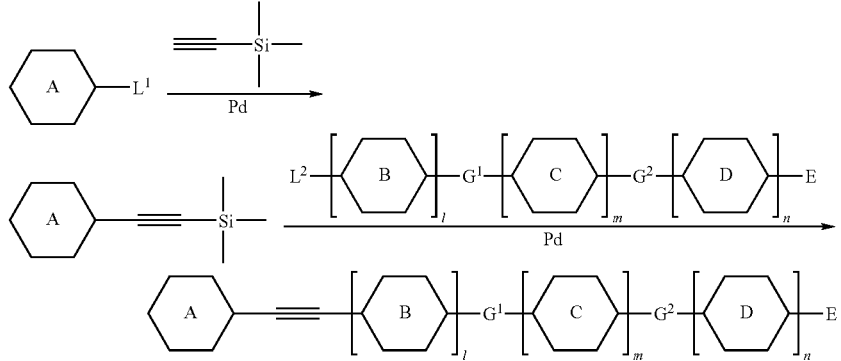

wherein ring A, ring B, ring C, ring D, l, m, n, $G^1$, $G^2$, and E are same as defined in claim 11, and each of $L^1$ and $L^2$ independently represents halide, mesylate, tosylate, or triflate.

15. The resin composition as claimed in claim 11, wherein the compound is prepared by Reaction Scheme 2:

[Reaction Scheme 2]

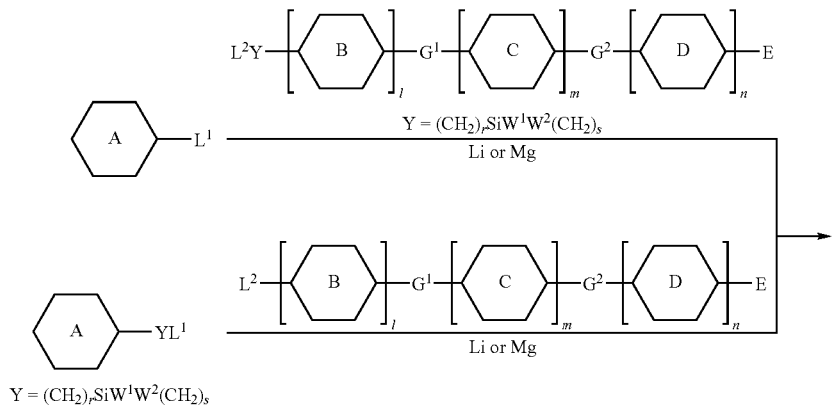

Y = $(CH_2)_rSiW^1W^2(CH_2)_s$

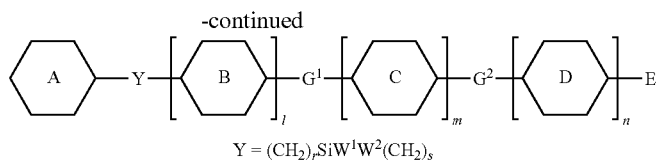

wherein ring A, ring B, ring C, ring D, l, m, n, $W^1$, $W^2$, r, s, $G^1$, $G^2$ and E are same as defined in claim 11, and each of $L^1$ and $L^2$ independently represents halide, mesylate, tosylate, or triflate.

16. The resin composition as claimed in claim 11, wherein the compound is prepared by Reaction Scheme 3:

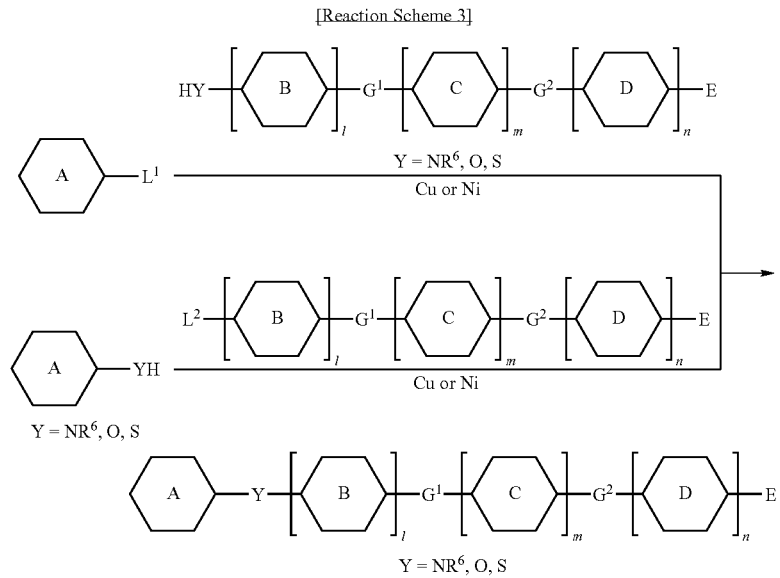

wherein ring A, ring B, ring C, ring D, l, m, n, $G^1$, $G^2$, $R^6$ and E are same as defined in claim 11, and $L^1$ represents halide, mesylate, tosylate, or triflate.

17. The resin composition as claimed in claim 11, wherein the compound is prepared by Reaction Scheme 4:

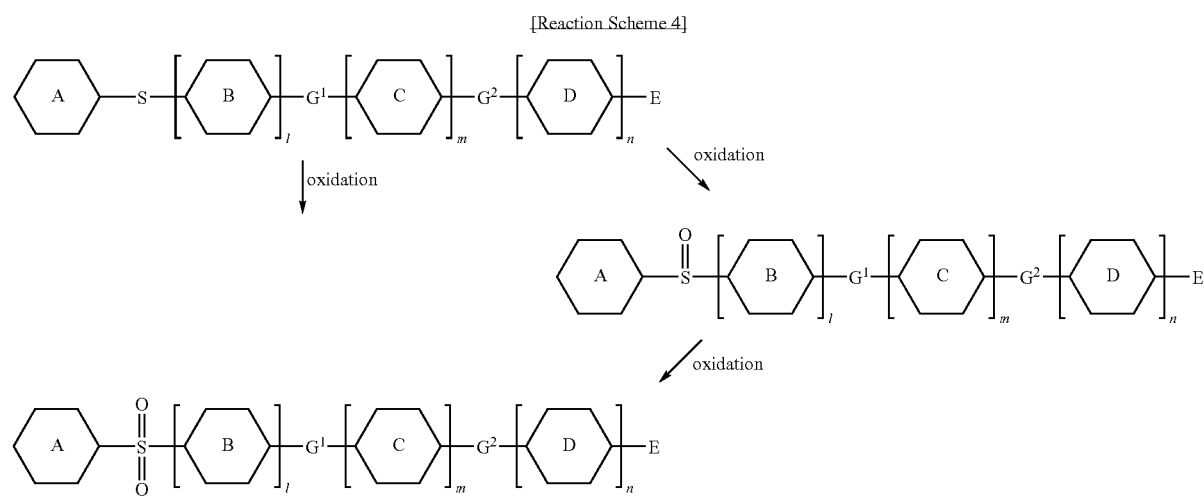

wherein ring A, ring B, ring C, ring D, l, m, n, $G^1$, $G^2$ and E are same as defined in claim 11.

18. The resin composition as claimed in claim 11, wherein the compound is prepared by Reaction Scheme 5:

[Reaction Scheme 5]

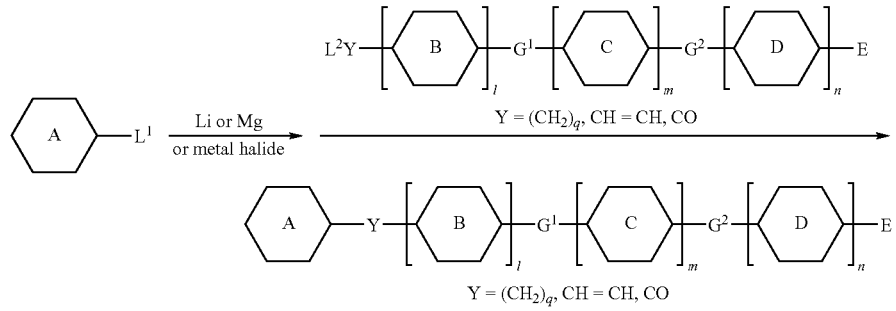

wherein ring A, ring B, ring C, ring D, l, m, n, q, $G^1$, $G^2$ and E are same as defined in claim 11, and each of $L^1$ and $L^2$ independently represents halide, mesylate, tosylate, or triflate.

19. The resin composition as claimed in claim 11, wherein the compound is prepared by Reaction Scheme 6:

[Reaction Scheme 6]

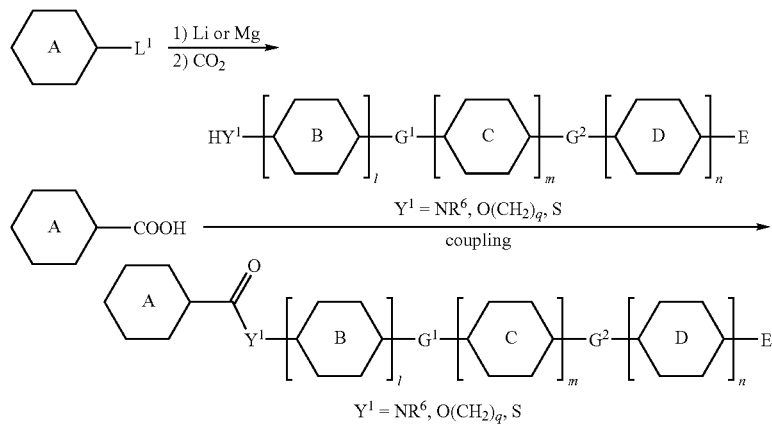

wherein ring A, ring B, ring C, ring D, l, m, n, q, $G^1$, $G^2$, $R^6$ and E are same as defined in claim 11, and $L^1$ represents halide, mesylate, tosylate, or triflate.

20. The resin composition as claimed in claim 11, wherein the compound is prepared by Reaction Scheme 7:

[Reaction Scheme 7]

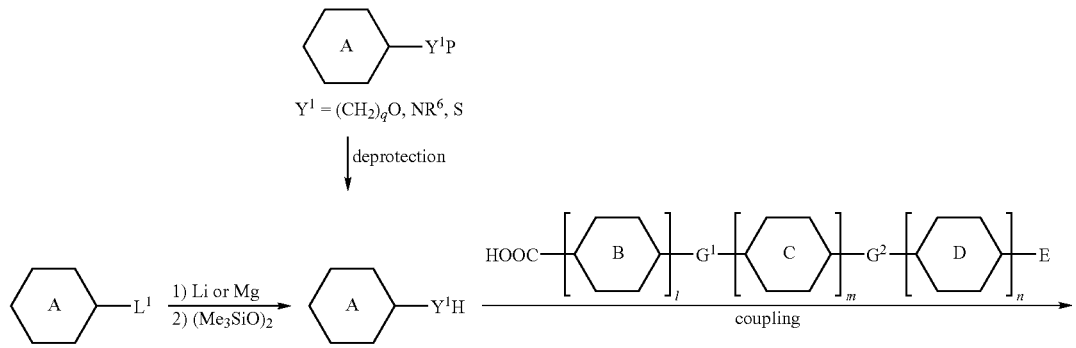

-continued
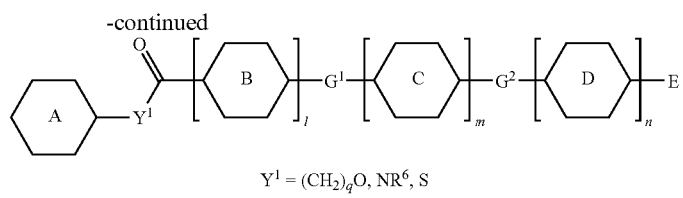
$Y^1 = (CH_2)_qO, NR^6, S$
wherein ring A, ring B, ring C, ring D, l, m, n, q, $G^1$, $G^2$, $R^6$ and E are same as defined in claim 11, $L^1$ represents halide, mesylate, tosylate, or triflate, and P represents a protection group.
* * * * *